United States Patent
Weers et al.

(10) Patent No.: US 8,748,497 B2
(45) Date of Patent: Jun. 10, 2014

(54) OPTIMIZED FLUOROCARBON EMULSIONS FOR BLOOD SUBSTITUTES AND OTHER THERAPEUTIC USES

(75) Inventors: Jeffry Weers, Belmont, CA (US); David Klein, Olympia, WA (US); Cindy Johnson, Rancho Santa Margarita, CA (US)

(73) Assignee: Alliance Pharmaceutical Corp., San Diego, CA (US)

( * ) Notice: Subject to any disclaimer, the term of this patent is extended or adjusted under 35 U.S.C. 154(b) by 1436 days.

(21) Appl. No.: 12/227,502

(22) PCT Filed: May 22, 2007

(86) PCT No.: PCT/US2007/012286
§ 371 (c)(1),
(2), (4) Date: May 24, 2010

(87) PCT Pub. No.: WO2007/139827
PCT Pub. Date: Dec. 6, 2007

(65) Prior Publication Data
US 2010/0298445 A1    Nov. 25, 2010

Related U.S. Application Data

(60) Provisional application No. 60/802,339, filed on May 22, 2006.

(51) Int. Cl.
*A61K 31/02* (2006.01)
*A61P 7/00* (2006.01)

(52) U.S. Cl.
USPC .......... 514/757; 514/759; 514/772; 514/832; 424/9.52

(58) Field of Classification Search
USPC ......... 514/757, 743, 759, 772, 832; 424/9.52; 516/53
See application file for complete search history.

(56) References Cited

U.S. PATENT DOCUMENTS

| | | | | |
|---|---|---|---|---|
| 4,927,623 | A | * | 5/1990 | Long, Jr. ................... 424/9.52 |
| 2004/0068020 | A1 | * | 4/2004 | Weers et al. ................. 516/53 |

* cited by examiner

*Primary Examiner* — Savitha Rao
(74) *Attorney, Agent, or Firm* — Kevin S. Helmbacher

(57) ABSTRACT

The present invention is directed to a stable fluorocarbon emulsion having a continuous aqueous phase and discontinuous fluorocarbon phase comprising two fluorocarbons and surprisingly demonstrates that perfluorodecyl bromide is as effective in stabilizing perfluorooctyl bromide emulsions of certain concentrations than much more highly concentrated perfluorooctyl bromide/perfluorodecyl bromide emulsions without the significant problems experienced in higher concentrated emulsions such as longer organ retention times, formation of PFDB crystals, larger emulsion particles, manufacturing problems and inability of repeat dosing inherent with higher concentrations of perfluorodecyl bromide.

11 Claims, 8 Drawing Sheets

OPTIMIZED FLUOROCARBON EMULSIONS FOR BLOOD SUBSTITUTES AND OTHER THERAPEUTIC USES

RELATED APPLICATIONS

This application claims priority of U.S. Provisional Patent Application No. 60/802,339 filed on May 22, 2006.

FIELD OF USE

The present invention relates to fluorocarbon and perfluorocarbon emulsions optimally formulated for use in human patients as an oxygen carrier for blood and prevention of exposure to homologous or allogeneic blood and other therapeutic uses. More particularly, the present invention is directed to fluorocarbon emulsion formulations having a continuous aqueous phase and a discontinuous fluorocarbon phase displaying optimal stability with minimal organ retention, thereby avoiding undesirable side-effects.

BACKGROUND OF THE INVENTION

Blood is a complex dispersion of colloidal particles (e.g., red and white blood cells, proteins, etc.) in an acellular continuous plasma phase. The components of the disperse phase of blood provide most of the biological functions including oxygen transport to tissues, hemostasis, host defense, transport of nutrients and hormones, and the removal of metabolic wastes. Although all of the functions of blood are important, the quintessential function of blood is the delivery of oxygen. Oxygen deprivation or ischemia quickly leads to irreversible degradation of cells, tissues and organs.

Currently, human blood is the agent of choice for acutely and chronically anemic patients. However, donated blood is not without its risks. Donated blood may be contaminated by a large number of pathogens, such as the human immunodeficiency virus (HIV), hepatitis or prions which cause variant Creutzfeldt-Jakob disease. Transfusion of allogeneic blood can also result in immunosuppression which has been linked to increased recurrence of cancer and incidents or postoperative infections in surgical patients. Blumberg et al., *Blood*, 66 Supp. 1, 274a (1966); Maetani et al., *Ann. Surg*, 203, 275 (1986).

Although the public's perception of risk focuses on risk of infection, clerical errors leading to mistransfusion are the most common causes of serious morbidity and mortality related to blood transfusion. The reported incidence of administration of RBCs to other than the intended recipient is 1 in 19,000; however, an actual incidence of 1 in 400 units was found in a prospective study of transfusion errors. American Association of Blood Banks, *Noninfectious Serious Hazards of Transfusion*, Association Bulletin, 01-4 (2001). During storage of blood, biochemical and morphologic changes occur in the blood that results in irreversible RBC damage and reduced post transfusion survival. This so-called "storage lesion" causes depletion of 2,3-diphosphoglyceric acid (2,3-DPG), resulting in less efficient oxygen transport by hemoglobin until naturally repleted, a process taking many hours. Valeri et. al, "Restoration in vivo erythrocyte adenosine triphosphate, 2,3 diphosphoglycerate, potassium ion and sodium ion concentrations following transfusion of acid-citrate-dextrose-stored human red blood cells." *J. Lab Clin Med.*, 73:722-33 (1969). Stored blood also contains bioreactive substances such as cytokines, which are implicated as a primary cause of nonhemolytic febrile transfusion reactions.

While disease transmission and clerical error remain serious issues for blood transfusion, the availability of donor blood has recently emerged as a significant concern on an international level. Concern over blood shortages appears to be driven in part by recent guidelines to defer blood donors who have spent extended periods of time in Europe, due to the potential risk of contracting variant Creutzfeldt-Jakob Disease (vCJD) from consumption of infected beef. In addition, a decreasing blood donor pool (due to an aging population and greater donor restrictions) and an increasing demand for blood for major surgical procedures in a larger number of elderly patients are resulting in frequent regional shortages causing cancellations or delays in elective surgery. Donor blood, when administered, is often old and must be typed and crossmatched for each patient, a process which can result in dangerous transfusion delays. Blood must also be refrigerated and has a shelf life of approximately 42 days, making it unavailable in many critical instances such as trauma situations in remote areas. Shortage of stored blood is a significant worldwide problem with blood stocks only having a several day supply in many cases, making coping with a disaster very difficult.

The search for therapeutic agents to replace the oxygen transport function of blood continues to be a high priority throughout the world. The goal is to find a replacement to donor blood which is pathogen free, stable, storable for long periods of time, affordable, and a universal donor product that would be immediately available when and where it is needed. Currently, there are two diverse approaches being undertaken in blood substitutes, purified hemoglobin derivatives and fluorochemical emulsions.

1. Purified Hemoglobin Based Oxygen Delivery

Efforts have been underway for some time to produce hemoglobin based oxygen carriers. Hemoglobin is a tetrameric protein of approximately 64,000 daltons which carries oxygen throughout the body. Hemoglobin is composed of four subunit polypeptide chains of about 140 amino acids each. Each chain has a molecular mass of 16,100 daltons and carries a tetrapyrrole iron-containing prosthetic group, heme, which can bind to one molecule of oxygen. In humans there are several different types of hemoglobins and all types contain four subunits. The differences in hemoglobin subtypes in humans are limited to the primary structure (amino acid sequence) of globin.

Blood transports oxygen bound to hemoglobin within the red blood cells which distribute oxygen throughout the tissues. Consequently, hemoglobin's ability to bind and release oxygen has made it an attractive subject for a blood substitute. However, hemoglobin is an inherently unstable molecule. Outside of its red blood cell environment, the hemoglobin molecule rapidly dissociates into dimers composed of an alpha and a beta subunit which are rapidly removed from circulation by the kidneys. Thus, development of a suitable stroma free hemoglobin molecule depends on the development of a stable, functional tetramer of hemoglobin which does not dissociate into dimers upon infusion. Another problem of hemoglobin outside of its red blood cell environment is caused by its having a high oxygen affinity (due to the lack of its normal allosteric effector, 2,3-diphosphoglycerate normally present in red blood cells) and the potential in high concentrations to cause renal tubular obstruction and consequent renal failure. Thus, in order to be an effective oxygen carrier in a cell-free state or in solution, hemoglobin must be chemically modified to avoid the problem of disassociation and oxygen affinity. Secondary goals are to produce a high yield of product in a cost effective manner.

Efforts to solve this problem have been undertaken in several novel ways including chemically binding the hemoglobin protein subunits together to prevent dissociation (e.g., by the binding of pyridoxal phosphate to the hemoglobin molecule or various other cross linking strategies) and the production of recombinant hemoglobin. Problems with chemically altering hemoglobin include ensuring an adequate supply of the raw hemoglobin material such as human blood which is in short supply. The use of hemoglobin obtained from other mammals, such as bovine derived hemoglobin, is a concern due to the bovine spongiform encephalitis virus and other pathogens. One alternative is recombinant hemoglobin. The problem with recombinant hemoglobin is its low yield and therefore its high cost of production. There are also purity concerns as endotoxin contamination is often a problem with *Escherichia coli* products Another problem of artificial hemoglobin is its binding of other free gases. Free hemoglobin avidly binds nitric oxide. It is unknown whether this in vivo binding is of clinical significance, although binding of nitric oxide has been implicated as the cause of hypertension commonly seen following hemoglobin infusion. It remains to be determined what effects stroma free hemoglobin has on regional autoregulation of blood flow, and whether the hypertension associated with hemoglobin infusion has pathophysiologic consequences. At present, little data are available in large animal or clinical studies utilizing these compounds to elucidate the importance of this phenomenon.

2. Fluorocarbon Emulsions

Fluorochemicals are molecules comprised of fluorine atoms. The term fluorochemical or fluorocarbon is contrasted with the term perfluorochemicals ("PFCs"), which are chemically inert synthetic molecules consisting primarily of carbon and fluorine atoms (i.e., no hydrogen atoms). Liquid PFCs and fluorocarbons are generally clear, colorless, and practically odorless, and possess the intrinsic ability to physically dissolve significant quantities of many gases, including oxygen, carbon dioxide and nitrogen. Because PFCs are hydrophobic, they are not miscible with water and therefore must be emulsified with a surfactant (e.g., phospholipid) to create an aqueous-based PFC emulsion for intravenous use. By mixing the PFC, surfactant and an aqueous buffer under high shear (e.g., homogenization) conditions, tiny submicron-sized droplets are formed in the aqueous media. The PFC droplets are surrounded by a monolayer of surfactant in which the hydrophobic lipid end of the surfactant molecules orient themselves into the PFC-containing core while the hydrophilic phosphate-containing polar head groups form the outer surface of the droplet where they are exposed to the aqueous environment.

PFCs and fluorocarbons do not deliver oxygen to tissues in the same manner as hemoglobin. Oxygen is highly soluble in fluorocarbon compounds, which, after intravascular injection, are present in the plasma phase of blood. Thus the contribution of fluorochemicals to oxygen delivery is due to their ability to increase $O_2$ carried in the plasma compartment. Although the absolute amount of $O_2$ carried by fluorocarbon compounds is relatively small, even at high inspired Fractional Oxygen Concentrations ($FiO_2$), a very high percentage of the transported $O_2$ is released at the tissues resulting in $O_2$ extraction from the fluorocarbon phase, often in excess of 90%.

PFC emulsions augment the total oxygen content of the blood by increasing the dissolved oxygen carried within the plasma compartment in an amount linearly proportional to the oxygen partial pressure ($PO_2$). At elevated levels of $PO_2$ (patient inspiring high concentrations of oxygen), oxygen within the PFC emulsion is more readily available to tissues than the oxygen bound to hemoglobin in red blood cells (RBCs). This is because oxygen from PFC emulsions load and offload linearly, whereas oxygen from red blood cells chemically bind and release according to the S-shaped oxyhemoglobin disassociation curve. Extraction of $O_2$ from hemoglobin at the tissues under normal circumstances is in the range of 20-25% and is lower overall than when fluorocarbon compounds are in the circulation delivering fluorocarbon-dissolved $O_2$ to the tissues.

Hemoglobin is nearly saturated at atmospheric oxygen levels and its oxygen content cannot be enhanced by any significant amount by increasing the inspired oxygen concentration. The extraction ratio for PFC emulsions is about 60% as compared to about 20-25% for hemoglobin under ambient conditions. When high concentrations of oxygen are inspired oxygen extraction from PFC emulsions reaches 90% or more. Consequently, when a fluorocarbon or PFC emulsion is present in the blood, the fluorocarbon or PFC emulsion will always release its oxygen load first, thus conserving the oxygen bound to hemoglobin. Numerous in vivo and in vitro studies support the efficacy of PFC emulsions for enhancement of oxygen delivery and maintenance or improvement of systemic and tissue oxygenation during surgical procedures.

Since the early 1960s, a number of different research efforts have attempted to develop a stable fluorocarbon emulsion for use as an intravascular oxygen therapeutic. The first commercial development of an injectable fluorocarbon emulsion was achieved approximately 30 years ago by the Green Cross Corporation (Osaka, Japan) with the production of FLUOSOL, a 20% w/v PFC emulsion comprising 14% w/v perfluorodecalin and 6% w/v perfluorotripropylamine, emulsified primarily with a synthetic poloxamer, Pluronic F-68 and a small amount of egg yolk lecithin. Limitations of this first generation product included the need for frozen storage of the stem emulsion, the need to thaw the emulsion and subsequently mix with two annex solutions prior to use. Short product stability after reconstitution (8 hours) and significant side effects (e.g., severe alternate pathway complement activation) were big problems for FLUOSOL which were primarily caused by the synthetic Pluronic surfactant.

FLUOSOL was tested extensively in severely anemic and actively bleeding Jehovah's Witness patients, and clearly demonstrated the ability to deliver oxygen. Tremper et al., "The preoperative treatment of severely anemic patients with a perfluorochemical oxygen-transporting fluid, Fluosol-DA."; *N Engl J Med* 307; 277-83 (1982); Gould et. al, "Fluosol-DA as a red-cell substitute in acute anemia." *N Engl J Med* 314: 1653-6 (1986).

FLUOSOL, however, did not receive FDA approval for this large-volume "blood substitute" indication because the temporary oxygenation benefit did not significantly improve mortality outcome in these bleeding and extremely anemic patients who refused blood transfusions due to their religious beliefs. Subsequent efforts to develop FLUOSOL focused on using it as an adjunct to coronary artery balloon angioplasty (PTCA) procedures, i.e., as an oxygen-carrying low-viscosity fluid that could be perfused through the PTCA catheter to oxygenate the distal myocardium during prolonged balloon inflation. Efficacy of FLUOSOL treatment during PTCA was clearly demonstrated based on attenuating myocardial ischemia, maintaining ventricular function (improved cardiac output) during balloon inflation and decreasing wall motion artifacts (i.e., decreased ST segment elevations and improved left ventricular ejection fraction). Bell et al., "Does intracoronary infusion of Fluosol-DA 20% prevent left ventricular diastolic dysfunction during coronary balloon angioplasty?"

*J Amer Coll Cardiol* 16: 959-66 (1990); Cowley et al., "Perfluorochemical perfusion during coronary angioplasty in unstable and high-risk patients." *Circulation* 81 (Supp IV): IV-27-34 (1990). These data formed the basis for FLUOSOL's marketing approval in the United States, which was granted by the FDA in December 1989. To date, FLUOSOL represents the only synthetic oxygen therapeutic approved by the FDA.

Additional clinical testing during the late 1980s and early 1990s occurred in cancer patients using FLUOSOL as an adjunct to primary radiation. These studies included patients with advanced head and neck malignancies, anaplastic astrocytomas, carcinoma of the lung and glioblastomas multiforme. In the early 1990s, FLUOSOL was also tested in a large multicenter clinical study (TAMI-9) in 430 patients with acute myocardial infarction, to assess the safety and efficacy of FLUOSOL as an adjunct reperfusion therapy following treatment with a thrombolytic agent (tissue-type plasminogen activator). A trend was observed for lower mean infarct size and less recurrent ischemia in the FLUOSOL-treated group. Unfortunately, significant improvement was not seen in global ejection fraction, regional wall motion or left ventricular ejection fraction. Due to the large volumes of FLUOSOL administered (15 mL/kg), a tendency for transient congestive heart failure and pulmonary edema was observed, which likely attenuated the oxygenation efficacy benefit of the FLUOSOL treatment.

Despite these efforts to develop secondary indications, Green Cross stopped manufacturing FLUOSOL in early 1994, primarily due to poor sales in the PTCA market (since autoperfusion catheters had since entered the market which now allowed blood to be perfused through the lumen of the catheter during balloon inflation). In addition, data had become available that prolonged balloon inflation times did not correlate with a decrease in the rate of coronary restenosis post-PTCA. Nevertheless, the FDA approval of FLUOSOL represented a very significant milestone in the development of oxygen therapeutics. This approval demonstrated that a PFC-based emulsion was both safe and efficacious as a temporary intravascular oxygen carrier to ameliorate hypoxia in ischemic tissues in patients.

During the last 10-15 years, commercial research efforts have resulted in the development of second-generation fluorocarbon emulsions with improved product characteristics compared to the first generation dilute formulations. The most successful of these efforts focused on more versatile linear chain fluorocarbon compounds (instead of cyclic fluorocarbon molecules) that have even slightly higher oxygen solubility. An additional improvement in these second-generation fluorocarbon emulsions involved the use of lecithin, i.e., egg yolk phospholipid (EYP), as the surfactant. EYP has been used for years to make parenteral products such as INTRALIPID (i.e., triglyceride-based fat emulsions for intravenous feeding of patients who cannot ingest food), and is much more biocompatible than the synthetic Pluronic-based surfactants used previously.

Another development effort to produce a fluorocarbon-based oxygen carrier has been on-going for many years in Russia, but relatively little information is available in the English literature for this product. PERFTORAN, originally developed at the Institute of Theoretical and Experimental Biophysics (Puschino, Russia), is a 20% w/v emulsion consisting of 14% w/v perfluorodecalin and 6% w/v perfluoro-n-methylcyclohexylpiperidine emulsified with a synthetic poloxamer (Proxanol) similar to Pluronic F-68. Average particle size in the PERFTORAN emulsion is <0.2 µm. However, the emulsion must be stored frozen (for up to 3 years), but after thawing it can be kept refrigerated for only 2 weeks. Perftoran has apparently been evaluated in more than 500 patients across a wide variety of different clinical and medical indications including battlefield use on soldiers suffering from traumatic blood loss. Vorobyev et al., "Perfluorocarbon emulsion Perftoran—The plasma substitute with gas transporting function." *Artif Cells Blood Subst Immob Biotech* 24: 453 (1996).

In Russia, PERFTORAN was approved in 1999 for human use. The indication statement for PERFTORAN claims that it is to be used "as a blood substitute preparation with gas transporting function in case of shock, blood losses, multiple trauma, burning of large surface of skin, conditions of apparent death, as well as in transplantology." It has also been used clinically in cardiopulmonary bypass, in regional perfusion to treat limb ischemia, and for severe alcohol intoxication. It is noteworthy, however, that no studies with PERFTORAN have ever been performed outside of Russia, reportedly due to their inability to manufacture the product according to cGMP guidelines.

Synthetic Blood International, Inc. (SBI) has been working for many years on PFCs, based on the early pioneering work of Leland Clark Jr. The initial focus of this company was to develop an implantable glucose biosensor for diabetics, and to utilize PFCs for liquid ventilation (Fluorovent). Only in the past few years, has SBI formulated a concentrated 60% w/v PFC emulsion apparently based on a custom-synthesized $C_{10}F_{20}$ proprietary PFC molecule. This compound is claimed to possess physical properties that are favorable for making biocompatible PFC emulsions for in vivo use. However, their proprietary compound is likely difficult to synthesize at very high levels of purity, and is probably expensive to produce since it requires a custom synthesis. Also, the tissue residence time will likely be longer than other more commonly used PFCs, such as pefluorodecalin or perflubron. In February 2003, SBI announced the filing of their IND for OXYCYTE, and received FDA approval to start a dose-escalation Phase 1 study in April 2003.

In the early 1990s, Hemagen/PFC (St. Louis, Mo.) attempted to use a custom-synthesized fluorochemical, perfluorodichlorooctane ($C_8F_{16}Cl_2$; PFDCO) when they attempted to develop OXYFLUOR as a concentrated emulsion. Kaufman R J. "Clinical development of perfluorocarbon-based emulsions as red cell substitutes." *Blood Substitutes: Physiological Basis of Efficacy*. Boston: Birkhauser, 52-75 (1996). Hemagen/PFC attempted a novel approach by adding oil to the emulsion in order to decrease the particle size of their OXYFLUOR emulsion and thereby increase product stability. The resulting OXYFLUOR emulsion was a 3-phase formulation based on combining PFDCO with triglyceride (safflower oil) and EYP as the only surfactant (78% w/v (40% v/v) fluorocarbon emulsion). The OXYFLUOR emulsion had an average particle size of 0.22-0.25 µm, but actually consisted of two populations of different particles; i.e., small oil (triglyceride) droplets and larger PFC-containing droplets. As a result, the side effect profile in humans was more pronounced, causing significant febrile reactions and flu-like symptoms due to the acute phase reaction triggered by these larger sized emulsion particles. Kaufman R. "The results of a Phase 1 clinical trial of a 40% v/v % emulsion of HM351 (Oxyfluor™) in healthy human volunteers." *Artif Cells Blood Subst Immob Biotech;* 22: A112 (1994).

Hemagen was pursuing an indication to ameliorate the cognitive dysfunction that is commonly encountered post-bypass, which is presumably due to local cerebral ischemia caused in part, by gaseous microemboli generated during cardiopulmonary bypass. An early stage Phase 2a safety study in cardiopulmonary bypass was initiated, but all patients had to be pretreated with dexamethasone to suppress the acute side effect profile. This ultimately led to the demise of these clinical studies, and development was ultimately stopped.

Despite the problems of various fluorocarbon emulsions as described, depending on the choice of specific PFC and surfactant, it is possible to make stable fluorocarbon-in-water emulsions for in vivo use in humans with exceptionally small particles (median diameter<0.2 µm) which remain stable over time and are biocompatible. However, the selection of a particular fluorocarbon(s) with the appropriate physical and chemical properties, in the proper concentrations and amounts, and the proper surfactant, is critical in determining how safe (i.e., biocompatible) a fluorocarbon emulsion will be in vivo, and how readily the fluorocarbon molecules will be eliminated from the body. Inadequate purity of a fluorocarbon, that contains other fluorocarbon compounds or partially fluorinated contaminants, can adversely affect the safety of the fluorocarbon emulsion and often results in toxicity. Fluorocarbon characteristics like molecular weight, lipid solubility, and vapor pressure are all major factors that directly influence the behavior of fluorocarbons in vivo. In addition, these fluorocarbon properties and the selection of an appropriate surfactant for use with the fluorocarbons, with the right chemical and physical properties, ultimately determines the intrinsic stability and shelf life of the final fluorocarbon emulsion formulation.

Pharmacokinetics of Intravenously Administered Fluorocarbon Emulsions

The pharmacokinetics of intravenously administered fluorochemical emulsions may be described by the four compartment illustration in FIG. 1. Emulsion droplets are cleared from the circulation through phagocytosis by circulating monocytes or tissue resident macrophages of the reticuloendothelial system ("RES"). Circulating monocytes pass through the pulmonary circulation and phagocytize emulsion droplets in the circulation, then migrate to the alveolar space where the fluorochemical is transported across the blood/air interface and eliminated in expired air. The rate constant for this process, $k_{10}$, has been shown to be very small indicating that little fluorocarbon is removed by this pathway. The dominant blood removal mechanism involves uptake and phagocytosis of the droplets by the cells of the RES. Approximately 80% or more of the administered dose is found in the organs of the RES after removal from the blood, principally the liver and spleen.

Chemically and biologically perfluorocarbons are inert and thus no metabolism is observed for perfluorochemicals. Following phagocytosis, intracellular fluorochemical is removed from RES cells (k24) by incorporation in circulating lipid carriers (i.e., chilomicrons and lipoproteins). At this point the fluorochemical can be eliminated in expired air (k40), partitioned into adipose tissue (k43) or returned to the RES (k42). The ultimate removal depends on the magnitude of the rate constants which populate and depopulate compartment 4. The rate determining step, k24, is controlled by the mass transfer of fluorochemical into the lipid carriers, a process which depends critically upon the lipid solubility of the fluorochemical. R. E. Moore and L. C. Clark in R. Frey et al., "Oxygen Carrying Colloidal Blood Substitutes: $5^{th}$ Int. Symp. On Perfluorochemical Blood Substitutes, Munich, Germany," pg. 50 (1982). The concentration of fluorochemical found in compartment 3 (adipose tissue) is also dependent on the lipophilic nature of the fluorochemical. Because adipose is poorly perfused, the removal will be slow compared to the RES which has a rich circulation. The redistribution into adipose leads to a decrease in the whole body removal rate (k40). For a typical fluorochemical (e.g., perfluorooctyl bromide), the rate constants have the following magnitude in units of $hr^{-1}$: k10≈0.000, k12≈0.04, k24≈0.006, k42≈0.002, k34≈0.002, k40≈0.07.

The nature of the fluorochemical can have profound effects on the observed pharmokinetics. As discussed, k24 depends primarily on the lipophilicity of the fluorochemical. Indeed, significant differences in k24 have been observed for the two fluorochemical components of the fluorocarbon emulsion FLUSOSOL, a fluorocarbon emulsion approved by the United States Food and Drug Administration to deliver oxygen to tissues during balloon angioplasty procedures (The Green Cross Corp., Osaka, Japan). The rate constants for RES elimination (k24) are equal to 0.10 and 0.011 $day^{-1}$ for F-decalin and F-tripropylamine, respectively, and body clearances are much slower than for perfluorooctyl bromide.

The intravascular persistence of the fluorochemical is also an important factor in its biocompatibility since it is directly proportional to the efficacy of an emulsion product designed for use in "blood substitute" applications. The magnitude of k12 (uptake of particles by the RES) depends critically on the total dose of fluorochemical, the emulsion droplet size, and possibly the binding of specific opsonins or dysopsonins which promote droplet recognition by the RES, or alternatively give "stealth-like" characteristics to the emulsion droplets. In fluorochemical emulsions containing two phase disperse phase components, significant partitioning of the fluorochemical components is observed between different sized droplets due to molecular diffusion of the more water soluble components through the continuous phase. This leads to a situation where the more water soluble fluorochemical is concentrated in the larger droplets, while the smaller droplets are enriched in the slower diffusing insoluble component. Since different sized droplets have different fluorochemical quantities, it is possible to imagine a situation where the individual rate constants for removal from the blood might differ somewhat, especially as the larger sized droplets are selectively removed by the RES.

More direct evidence of the importance of fluorochemical lipophilicity in the removal process comes from the work of Obraztsov et al. who proposed a two step removal mechanism of perfluorochemicals. According to the model, the first step is the molecular diffusion of perfluorochemicals through the cytoplasm of the RES cells to the blood stream. This process occurs in a time span of minutes to hours. The second (rate-determining) step involves the mass transfer of fluorochemical from the RES organs to the lungs by the lipid carriers, a process which depends critically on PFC lipophilicity. In an elegant experiment, Obraztsov found that the organ retention time of perfluorochemicals can be decreased significantly by post-intravenous injection of a lipid emulsion given following PFC emulsion administration. The lipid emulsion is therefore able to provide a lipid sink in the blood to remove the PFC from the organs and carry it to the lungs. Obratzsov, V. V et. al, *J. Fluorine Chem.* 54, 376 (1991).

Stability of Fluorocarbon Emulsions

Submicron fluorochemical emulsions designed for oxygen transport are thermodynamically unstable. The primary mechanism of irreversible droplet coarsening is Ostwald ripening. J. G. Reiss, *Colloids Surfaces,* 84, 33 (1994). Ostwald ripening occurs as a consequence of the Kelvin effect, whereby small differences in surface tensions between different size droplets leads to growth of the larger droplets and shrinkage of the smaller ones with time. Mass transfer between droplets occurs via molecular diffusion of the disperse phase through the continuous phase. Ostwald ripening can occur not only after the emulsion is made during storage but also during the manufacturing process. To counteract emulsion coarsening via Ostwald ripening, Haguchi and Misra proposed the addition of a higher molecular weight second disperse phase component which is less insoluble in the continuous phase. Higuchi et al., *J. Pharm. Sci*, 51, 459 (1962). In this case, significant partitioning of the two disperse phase components between different droplets occurs, with the component having low water solubility being concentrated in the smaller droplets.

During Ostwald ripening in two component phase systems, equilibrium is established when the difference in chemical potential between different sized droplets, which results from capillary effects, is balanced by the difference in chemical potential resulting from partitioning of the two components (similar to Raoult's law for vapor/liquid equilibria).

The initial droplet size and distribution, droplet stability, and ultimately many of the observed side-effects found for fluorochemical emulsions, depend critically upon reducing Ostwald ripening. The physical stability of fluorocarbon emulsions, therefore, depends critically on the nature of the dispersed fluorocarbon phase.

The kinetics of droplet growth via molecular diffusion is most often described in terms of the Lifshitz-Slezov-Wagner ("LSW") theory. LSW theory relates that for a single component disperse phase, the cube of the mean radius increases linearly with time at a rate, $\bar{\omega}$.

$$\bar{\omega} = d/dt(a)^3 = 8\gamma V C_a D/9RT$$

where a is the radius, $\gamma$ is the interfacial tension, V is the molecular volume, $C_a$ is the water solubility, D is the diffusion coefficient, R is the molar gas constant, and T, the absolute temperature. Of particular importance for fluorocarbon emulsion stability is the water solubility term, a parameter which depends critically on the molecular weight of the fluorocarbon. In general, fluorocarbons with higher molecular weights exhibit reduced water solubility, and hence, greater emulsion stability. However, fluorocarbon emulsions destined as injectable oxygen carriers (i.e. blood substitutes) must also be biocompatible. Of particular importance is the half-life of the fluorocarbon in the organs of the RES. Although higher molecular weight fluorocarbons exhibit enhanced emulsion stability, they are also retained in the RES for extremely long periods of time.

Ostwald ripening may be decreased by inclusion of a secondary fluorochemical of higher molecular weight and lesser water solubility or a fluorinated surfactant which significantly reduces the interfacial tension at the fluorocarbon/water interface. Unfortunately, the addition of less water soluble secondary fluorocarbons to a formulation leads to increases in organ retention, a very serious side effect, since the fluorochemical's solubility in circulating lipid carriers will also be reduced. Fluorinated surfactants have proven to have serious toxicity issues making them risky as an emulsion stabilizer. In order to overcome the emulsion stability/organ retention dilemma, a secondary fluorocarbon must be chosen which provides the required emulsion stability/organ retention characteristics, is biocompatible with short organ retention times, and added in the smallest quantities possible while obtaining the needed benefit in stability. For this to occur, the chosen fluorochemical should be lipophilic (e.g., perfluorodecyl bromide). Nonlipophilic compounds (e.g. F-tripropylamine and F—N-methylcyclohexylpeperidine) are excreted too slowly and may not effectively stabilize fluorochemical emulsions.

Some representative primary and secondary fluorocarbons are included in the list below.

1. Primary Fluorocarbon

The primary fluorocarbon is selected for its short organ retention time and biocompatibility. In general, the half life in organs is preferably less than about 4 weeks, more preferably less than about 2 or 3 weeks, and most preferably 7 days or less. The molecular weight is from about 460 to about 550 daltons.

Such possible primary fluorocarbons include bis(F-alkyl) ethenes such as $C_4F_9CH=CHC_4F_9$ ("F-44E"), 1-$CF_3CF_9CH=CHC_6F_{13}$ ("F-i36E"), and cyclic fluorocarbons, such as $C_{10}F_{18}$ (F-decalin, perfluorodecalin or FDC); F-adamantane (FA); perfluoroindane; F-methyladamantane (FMA); F-1,3-dimethyladamantane (FDMA); perfluoro-2,2,4,4-tetramethylpentane; F-di- or F-tri-methylbicyclo[3,3,1] nonane (nonane); $C_{7-12}$ perfluorinated amines, such as F-tripropylamine, F-4-methyloctahydroquinolizine (FMOQ), F-n-methyl-decahydroisoquinoline (FMIQ), F-n-methyldecahydroquinoline (FHQ), F-n-cyclohexylpyrrolidine (FCHP), and F-2-butyltetrahydrofuran (FC-75 or RM101).

Other examples of primary fluorocarbons include brominated perfluorocarbons, such as perfluorooctyl bromide ($C_8F_{17}Br$, USAN perflubron), 1-bromopentadecafluoroheptane ($C_7F_{15}Br$), and 1-bromotridecafluorohexane ($C_6F_{13}Br$, also known as perfluorohexyl bromide or PFHB. Other brominated fluorocarbons are disclosed in U.S. Pat. Nos. 3,975,512 and 4,987,154 to Long and U.S. Pat. Nos. 5,628,930 and 5,635,538, which are hereby incorporated by reference in their entireties.

Also contemplated are fluorocarbons having other non-fluorine substituents, such as 1-chloro-heptadecafluorooctane ($C_8F_{17}Cl$, also referred to as perfluorooctyl chloride or PFOCl); perfluorooctyl hydride, and similar compounds having different numbers of carbon atoms.

Additional first fluorocarbons contemplated in accordance with this invention include perfluoroalkylated ethers, halogenated ethers (especially brominated ethers), or polyethers, such as $(CF_3)_2CFO(CF_2CF_2)_2OCF(CF_3)_2$; $(C_4F_9)_2O$. Further, fluorocarbon-hydrocarbon compounds may be used, such as, for example compounds having the general formula $C_nF_{2+1}$—$C_nH_{2n'+1}$; $C_nF_{2n+1}OC_nH_{2n'+1}$ or $C_nF_{2n+1}CH=CHC_nH_{2n'+1}$, wherein n and n' are the same or different and are from about 1 to about 10 (so long as the compound is a liquid at room temperature). Such compounds, for example, include $C_8F_{17}C_2H_5$ and $C_6F_{13}CH=CHC_6H_{13}$.

Other possible fluorocarbons for use as the primary fluorocarbon include perfluoroamines, terminally substituted linear aliphatic perfluorocarbons having the general structure:

$C_nF_{2n+1}R$, wherein n is an integer from 6 to 8 and R comprises a lipophilic moiety selected from the group of Br, Cl, I, $CH_3$, or a saturated or unsaturated hydrocarbon of 2 or 3 carbon atoms, bis(F-alkyl)ethenes having the general structure:

$C_nF_{2n+1}$—CH=CH—$C_{n'}F_{2n'+1}$, wherein the sum of n and n' equals 6 to 10, and perfluoroethers having the general structure:

$C_nF_{2n+1}$—O—$C_{n'}F_{2n'+1}$, wherein the sum of n and n' equals 6 to 9.

In addition, fluorocarbons selected from the general groups of perfluorocycloalkanes or perfluoroalkyl-cycloalkanes, perfluoroalkyl saturated heterocyclic compounds, or perfluorotertiary amines may be suitably utilized as the first fluorocarbon. See generally Schweighart, U.S. Pat. No. 4,866,096, which is hereby incorporated by reference in its entirety.

It will be appreciated that esters, thioethers, and other variously modified mixed fluorocarbon-hydrocarbon compounds, including isomers, are also encompassed within the broad definition of fluorocarbon materials suitable for use as the first fluorocarbon of the present invention. Other suitable mixtures of fluorocarbons are also contemplated.

Additional fluorocarbons not listed here, but having the properties described in this disclosure that would lend themselves to therapeutic applications, are also contemplated. Such fluorocarbons may be commercially available or specially prepared. As will be appreciated by one skilled in the art, there exist a variety of methods for the preparation of fluorocarbons that are well known in the art. See for example, Schweighart, U.S. Pat. No. 4,895,876, which is incorporated by reference in its entirety.

2. The Secondary Fluorocarbon

The secondary fluorocarbon can be an aliphatic fluorocarbon substituted with one or more lipophilic moieties and having a higher molecular weight than the first fluorocarbon. The lipophilic moiety may be terminally substituted on the fluorocarbon molecule. Preferably, the molecular weight of the second fluorocarbon is greater than about 540 Daltons. Constraints on the upper limit of the molecular weight of the second fluorocarbon are often related to its organ retention time and its ability to be solubilized by the first fluorocarbon. Most preferred second fluorocarbons have boiling points greater than about 150° C. and water solubilities of less than about $1 \times 10^{-9}$ moles/liter.

Of course, as will be appreciated by one skilled in the art, many fluorocarbons substituted with different lipophilic groups could be suitably used as the second fluorocarbon in the present invention. Such fluorocarbons may include esters, thioethers, and various fluorocarbon-hydrocarbon compounds, including isomers. Mixtures of two or more fluorocarbons satisfying the criteria set forth herein are also encompassed within the broad definition of fluorocarbon materials suitable for use as the second fluorocarbon of the present invention. Fluorocarbons not listed here, but having the properties described in this disclosure that would lend themselves to therapeutic applications, are additionally contemplated.

The lipophilic moiety is optimally selected from the group consisting of Br, Cl, I, $CH_3$, or a saturated or unsaturated hydrocarbon of 2 or 3 carbon atoms. Consequently, preferred second fluorocarbons may be selected from the group of terminally substituted fluorocarbon halides as represented by the general formula:

$C_nF_{2n+1}X$ or $C_nF_{2n}X_2$, wherein n is 8 or greater, preferably 10 to 12, and X is a halide selected from the group consisting of Br, Cl, or I;

1-alkyl-perfluorocarbons or dialkylperfluorocarbons as represented by the general formula:

$C_nF_{2n+1}$—$(CH_2)_{n'}CH_3$ wherein n is 8 or greater, preferably 10 to 12, and n' is 0 to 2;

1-alkenyl-perfluorocarbons as represented by the general formula:

$C_nF_{2n+1}$—$C_{n'}H_{(2n'-1)}$, wherein n is 10 or more, preferably 10 to 12, and n' is either 2 or 3; or brominated linear or branched perfluoroethers or polyethers having the following general structure:

Br—$(C_nF_{2n+1}$—O—$C_{n'}F_{2n'+1})$, wherein n and n' are each at least 2 and the sum of n and n' is greater than or equal to 8.

Most preferably, the second fluorocarbon of the present invention is selected from the group consisting of linear or branched brominated perfluorinated alkyl ethers, perfluorodecyl bromide ($C_{10}F_{21}Br$); perfluorododecyl bromide ($C_{12}F_{25}Br$); 1-perfluorodecylethene ($C_{10}F_{21}CH$=$CH_2$); and 1-perfluorodecylethane ($C_{10}F_{21}CH_2CH_3$); with perfluorodecyl bromide particularly preferred.

The question that must be asked of the particular secondary fluorocarbon is whether the increased stability provided by the secondary fluorocarbon is outweighed by the potential problems of prolonged organ retention time, and half-life, toxicity, biocompatibility and other complications.

The chemical formula of perfluorooctyl bromide ("PFOB") is $C_8F_{17}Br$. Its structure is $CF_3(CF_2)_6CF_2Br$ and the Chemical Abstract Service ("CAS") number is 423-55-2. Other physical parameters of PFOB include:

| | |
|---|---|
| Boiling point | 143° C. at 760 mm Hg |
| Vapor pressure | 10.5 mm Hg at 37° C. |
| Melting point | 4° C. |

The chemical formula of PFDB is $C_{10}F_{21}Br$. Its structure is $CF_3(CF_2)_8CF_2Br$. The CAS number is 307-43-7. Other physical parameters include:

| | |
|---|---|
| Boiling point | 180° C. at 760 mm Hg |
| Vapor Pressure | 1.5 mm Hg at 37° C. |
| Melting point | 55° C. |

The addition of perfluorodecyl bromide ("PFDB") to perfluorooctyl bromide ("PFOB") or perfluorodecalin ("FDC") emulsions has been found to result in excellent room temperature stability. Due to its lipophilic character, the half-life of PFDB in the RES is only 23 days, a value deemed acceptable for intravenous applications. The addition of PFDB is also found to result in narrow particle size distributions and fewer large particles. With the addition of PFDB to a PFOB emulsion, significant partitioning of the two components between different droplet sized droplets occurs as a consequence of molecular diffusion, whereby the insoluble component becomes concentrated in the smaller droplets, and the high solubility component enriches the larger droplets. The partitioning of the two components between different sized droplets leads to decreased solubility for the smaller droplets via Raoult's Law. This compensates for the difference in chemical potentials caused by differences in capillary pressures (i.e. the Kelvin effect). When the concentration balances the capillary effect, droplet growth ceases.

The emulsion growth rate $\omega_{ab}$, for a two component disperse phase is given by the following equation:

$$\omega_{ab} = 1/[(\Phi_a/\omega_a)+(\Phi_b/\omega_b)]$$

where $\Phi_a$ and $\Phi_b$ are the volume fractions of fluorocarbons a and b, respectively. $\omega_a$ and $\omega_b$ are the individual emulsion growth rates given by the above equation for fluorocarbons a and b.

While PFDB has proven to be an ideal candidate for a secondary fluorocarbon, PFDB should be formulated in amounts, with the appropriate primary fluorocarbon (e.g., PFOB) at appropriate concentrations, so as not to cause complications with organ retention and half-life, but still provide proper emulsion stability. Further, because there is a desire to use any fluorocarbon emulsion repeatedly on patients in as short time intervals as possible, the smallest amounts of PFDB should be used to allow for repeat doses. This should be in combination with the appropriate amount of primary fluorocarbon.

A further complication of PFDB being present in the emulsion in too high of a concentration is the significant risk of PFDB crystals forming in the emulsion due to its high melting point (55° C.). Crystallization of PFDB in the emulsion could cause serious safety and toxicity issues. There is also a significant manufacturing concern in that high concentrations of PFDB can easily crystallize when encountering cold spots in the manufacturing process. This is a serious consideration for formulating an emulsion, particularly at large scale manufacturing, in that should PFDB crystallize during the manufacturing process, because it is the emulsion stabilizer, it would not only present biocompatibility/toxicity issues but also its crystallization would make less PFDB available to stabilize the emulsion and the finished emulsion would be much less likely to meet product quality specifications. Another complication in PFDB being present in too high of a concentration is the risk of making particles too small, which can cause fluorocarbon particles to leak from the capillary beds into the interstitial space of tissues causing severe retention problems.

Thus, creating a usable fluorocarbon emulsion for in vivo use in humans requires the balancing of several critical considerations. A fluorocarbon emulsion designed for in vivo oxygen transport in humans should have at least the following attributes:

1. Acceptable organ half-life—The organ half-life of the fluorocarbon emulsion components should be as short as possible, preferably less than 4 weeks.
2. Acceptable shelf stability—The fluorocarbon emulsion should have a minimum of 6 months storage at 5° C., with 18 months of shelf life preferred. During the storage period, the physical characteristics and biocompatibility of the fluorocarbon emulsion should not change. Room temperature storage is preferred because of the added convenience, greater potential application and reduced expense;
3. Acceptable in vivo stability—The emulsion should not undergo phase changes, precipitation, coacervation, coalescence or other aggregative phenomena of an adverse physicochemical or biochemical nature when administered intravenously;
4. Excellent biocompatibility—The fluorocarbon emulsion should induce minimal side-effects and no toxic effects;
5. Acceptable or optimal particle size and distribution—The emulsion particle size plays an important role both due to size and distribution in toxicity, shelf life, side effects, and biodistribution and should therefore be within acceptable ranges;
6. Terminal sterilization—The emulsion should be of a physical characteristic to be able to be terminally sterilized;
7. Acceptable blood half-life—The emulsion should have a blood half-life which is acceptable for its intended purpose;
8. Acceptable viscosity—The viscosity of the whole blood/fluorocarbon emulsion mixtures is critical since tissue oxygenation and perfusion are inversely related to viscosity;
9. Low free fluoride values—The fluorocarbon should exhibit excellent chemical stability;
10. Surfactant safety—The surfactant should be biocompatible and non-toxic;
11. Acceptable fluorocarbon content—The biocompatibility and toxicity of a fluorocarbon depends critically on the total fluorocarbon content and must be efficacious in volumes acceptable to sick patients and should be formulated for repeat doses;
12. Manufacturing—The fluorocarbon emulsion should have physical properties which allow it to be easily manufactured and on a scaled up basis to produce consistent product. The fluorocarbons used in the formulation should be easily produced and with excellent purity; and,
13. Repeated dosage—The fluorocarbon emulsion should be able to be used repeatedly in as short of time intervals as possible for repeated dosing of patients.

SUMMARY OF THE INVENTION

The present invention is a fluorocarbon emulsion formulated as a result of extensive experimentation, analysis and a careful balancing of multiple factors in formulating a stabilized fluorocarbon emulsion ideally suited for in vivo use in humans for blood avoidance and other therapeutic uses. The preferred embodiment constitutes a fluorocarbon emulsion superior over prior art fluorocarbon emulsions in that has been formulated to maintain emulsion stability while achieving minimal organ retention time.

As stated above, molecular diffusion or Ostwald ripening has been shown to be the key determinant of initial particle size in fluorocarbon emulsions. Whereas droplet sizes of approximately 0.2 µm for short periods of time are achievable with perfluorooctyl bromide as the dispersed fluorocarbon phase, droplet sizes of less than 0.15-0.20 µm, which persist over long periods of time, may be achieved for mixtures of PFOB and PFDB of certain concentrations over long periods of time. PFDB, being virtually insoluble in the continuous aqueous phase but soluble in PFOB, serves to inhibit molecular diffusion by reducing the solubility of small droplets in the polydisperse dispersion. For PFOB at certain concentrations, it has been found that PFDB is a very effective particle growth retardant. PFDB is a linear, higher molecular weight analog of PFOB, the structure differing in having two additional carbon atoms and four additional fluorine atoms. The melting points of PFOB and PFDB are 4° C. and 55° C., respectively and the vapor pressures at 37° C. are 10.5 and 1.5 mm Hg, respectively.

The data herein surprisingly demonstrates that PFDB is as effective in stabilizing PFOB emulsions of particular concentrations when compared to much higher concentrations of PFOB/PFDB emulsions and that by using small amounts of PFDB (1-3% w/v of total emulsion) added to a 55-60% w/v PFOB emulsion, the same stabilization of the emulsion is achieved as occurs with mixtures of much higher concentrations of PFDB such as 90%/10% w/v PFOB/PFDB emulsions, 60%/30% w/v PFOB/PFDB emulsions and 60%/10% w/v PFOB/PFDB emulsions, without the significant problems experienced in these higher concentrated emulsions such as longer organ retention times, formation of PFDB crystals, larger emulsion particles, patient side-effects, manufacturing problems and inability of repeat dosing.

The retardation of particle size growth by the addition of small amounts of PFDB to certain concentrations of PFOB is dramatic and unexpected and the data herein demonstrates that if an optimal balance is struck with regard to amount versus effect, and biocompatibility versus stability, at concentrations of approximately 1%-3% w/v PFDB, with approximately 55%-60% w/v PFOB, up to a total fluorocarbon phase of approximately 59-62% w/v, emulsified with appropriate amounts of egg yolk phospholipid, an efficacious fluorocarbon emulsion is created which is ideally suited for in vivo oxygen delivery in humans.

The formulation of 58% w/v PFOB and 2% w/v PFDB is preferred, but other formulations such as 1, 2 and 3% w/v PFBD added to 55%, 56%, 57%, 58%, 59%, and 60% w/v PFOB, with all possible combinations, such as 55%-60% w/v PFOB/3% w/v PFDB, 55-60% w/v PFOB/2% w/v PFDB and 55-60% w/v PFOB/1% w/v PFDB are within the scope of the invention. Adding more PFDB, up to 10% w/v PFDB and beyond, offers little further benefit as to emulsion stability but creates significant problems as to biocompatibility, organ retention times and manufacturing issues.

The addition of smaller amounts of PFDB to a PFOB emulsion not only retards the rate of particle growth in the emulsion, but also allows for the initial formation of smaller particles after the emulsion is created. Creating smaller particles upon the formation of the emulsion results in a decrease in the number of inter-droplet contacts, which slows particle growth by coalescence and strengthens the EYP surface layer, to make fusion of the surfaces of contacting droplets more difficult. Smaller particles decrease inter-droplet contacts by slowing the phenomenon of sedimentation of fluorocarbon particles, so that the droplets are maximally separated. However, if particles are made too small, there is a significant risk of leakage of fluorocarbon particles from the capillary beds to the interstitial spaces between tissues. Thus a balance must be struck between creating particle sizes to reduce inter-droplet contacts, but not too small so as to cause leakage problems.

The velocity of sedimentation is given by Stokes Law (Ross and Morrison, *Colloidal Systems and Interfaces*, Wiley-Interscience, New York, pp. 69-125 (1988):

$$V = \frac{2r2(\rho_o - \rho_w)g}{9\eta}$$

where r=droplet radius
$\rho_o$=density of the oil
$\rho_w$=density of the water
$\eta$=viscosity The density of perflubron is 1.9 g/L, so the density term, $(\rho_o - \rho_w)$, encourages rapid sedimentation which would concentrate the particles in the bottom of the container. The rate of sedimentation, V, is decreased by decreasing droplet radius, which occurs when PFDB is added to perflubron. By increasing the ratio of PFOB to PFDB and due to the fact that PFDB is soluble in PFOB, more PFDB is carried away by the PFOB in the formulations described herein and there is less PFDB retained in the tissues of the patient. Further, the addition of smaller amounts of PFDB (1-3% w/v) to stabilize the PFOB emulsion will result in significant financial savings due to the high cost of PFDB, higher perfluorocarbon yields, less EYP required than is required for more concentrated PFDB emulsions and prolonged shelf life. The reduction in amount of EYP also leads to greater compatibility due to decreased levels of EYP resulting in less hydrolysis products such as excess free fatty acids and lysolecithin compounds in the emulsion.

The fluorocarbon emulsions described in the present application may be used in prevention of exposure of allogeneic blood in surgery and other situations where patients require blood. Although not limited to the following, some other therapeutic for the fluorocarbon emulsions of the present invention include its use in post-operative organ function (gut, liver, heart, brain, kidney), sickle cell anemia treatment, organ preservation, organ transplantation, enhancement of chemotherapy treatment, enhancement of radiation treatment, treatment of carbon monoxide poisoning, treatment of "the bends," traumatic brain injury and treatment in stroke. Although formulated for use in humans, the fluorocarbon emulsions of the present invention may be used in any mammal, bird, reptile or fish.

The present invention is directed, but not limited, to:

1) A storage stable fluorocarbon emulsion for in vivo oxygen delivery in human patients comprising a continuous aqueous phase and a discontinuous fluorocarbon phase, wherein the discontinuous fluorocarbon phase is comprised of the fluorocarbons perfluorooctyl bromide and perfluorodecyl bromide, wherein the perfluorooctyl bromide is present in the fluorocarbon emulsion at approximately 57-60% w/v of the total emulsion and the perfluorodecyl bromide is present in the emulsion at approximately 2-3% w/v of the total emulsion, and, the emulsion further comprising an emulsifying agent present in the amounts of approximately 3.5%-4% w/v.

2) The emulsion of paragraph 1 further comprising d,α-tocopherol.

3) The emulsion of paragraph 1 wherein the d,α-tocopherol is present in the amount of approximately 1% w/v.

4) The fluorocarbon emulsion of paragraphs 1, 2 and 3 further comprising NaCl, $NaH_2PO_4$ and EDTA.

5) The fluorocarbon emulsion of paragraphs 1 and 3 wherein the PFOB is present in the amount of 57-59% w/v and PFDB is present in the amount of 2% w/v.

6) The fluorocarbon emulsion of paragraphs 1, 2 and 3 wherein the PFOB is present in the amount of 58% w/v and the PFDB is present in the amount of 2% w/v.

7) The fluorocarbon emulsion of paragraph 1 wherein the emulsifying agent is egg yolk phospholipid present in the amount of approximately 3.6% w/v and further comprising NaCl, $NaH_2PO_4.H_2O$, $NaHPO_4.7H_2O$.

8) The fluorocarbon emulsion of paragraphs 1-4 wherein the fluorocarbon emulsion further comprises d,α-tocopherol and EDTA.

9) The fluorocarbon emulsion of paragraphs 1, 2, 3, 6 and 7 wherein d,α-tocopherol is present in 0.0025 w/v or less and EDTA is present in the amount of 0.02 w/v.

10) A fluorocarbon emulsion for oxygen transport to the tissues in humans and other mammals comprising: a continuous aqueous phase and a discontinuous fluorocarbon phase, wherein the discontinuous fluorocarbon phase consists of perfluorooctyl bromide and perfluorodecyl bromide, wherein the perfluorooctyl bromide is present in the fluorocarbon emulsion at approximately 57-60% w/v of the total emulsion and the perfluorodecyl bromide is present in the emulsion at approximately 1-3% w/v of the total emulsion.

11) The fluorocarbon emulsion of paragraph 10 further comprising an emulsifying agent consisting of egg yolk phospholipid present in the amount of approximately 3.5%-4% w/v.

12) The fluorocarbon emulsion of paragraph 10 wherein the emulsion is stabilized by a surfactant selected from the group consisting of fluorinated surfactants and lecithin based surfactants.

13) The fluorocarbon emulsion of paragraphs 10, 11 and 12 wherein the discontinuous phase consists of approximately 58-59% w/v PFOB and approximately 2-3% w/v PFDB.

14) The fluorocarbon emulsion of paragraphs 10, 11 and 12 wherein the discontinuous phase consists of approximately 58% w/v PFOB and 2% w/v PFDB.

15) The fluorocarbon emulsion of paragraphs 10 and 14 wherein upon formation of the emulsion, fluorocarbon particles of a median particle diameter of 0.18 μm or less are formed.

16) A fluorocarbon emulsion for oxygen transport to the tissues in humans and other mammals comprising: a continuous aqueous phase and a discontinuous fluorocarbon phase, wherein the discontinuous fluorocarbon phase consists of perfluorooctyl bromide and perfluorodecyl bromide, wherein the perfluorooctyl bromide is present in the fluorocarbon emulsion at approximately 58% w/v of the total emulsion and the perfluorodecyl bromide is present in the emulsion at approximately 2% w/v of the total emulsion.

17) The fluorocarbon emulsion of paragraph 16 further comprising a lecithin in the amount of approximately 3-4% w/v.

18) The fluorocarbon emulsion of paragraph 17 wherein the lecithin is egg yolk lecithin and is present in the amount of 3.6% w/v.

19) The fluorocarbon emulsion of paragraphs 16 and 18 further comprising an anti-oxidant.

20) The fluorocarbon emulsion of paragraph 19 wherein the anti-oxidant is d,α-tocopherol.

21). A fluorocarbon for in vivo use in humans comprising comprising a continuous aqueous phase and a discontinuous fluorocarbon phase, wherein the discontinuous fluorocarbon phase is comprised of the fluorocarbons perfluorooctyl bromide and perfluorodecyl bromide, wherein the perfluorooctyl bromide is present in the fluorocarbon emulsion at approximately 58% w/v of the total emulsion and the perfluorodecyl bromide is present in the emulsion at approximately 2% w/v of the total emulsion, and,
the emulsion further comprising an emulsifying agent present in the amounts of approximately 3.6% w/v.

22) The emulsion of paragraph 21 wherein the emulsifying agent is egg yolk phospholipid.

23) The emulsion of paragraphs 21 and 22 further comprising d,α-tocopherol in the amount of approximately 1% w/v.

24) The fluorocarbon emulsion of paragraphs 21 and 23 wherein the emulsifying agent is present in the amount of approximately 3.6% w/v and further comprising NaCl, $NaH_2PO_4.H_2O$, $NaHPO_4.7H_2O$.

25) The fluorocarbon emulsion of paragraphs 21, 22 and 24 wherein the fluorocarbon emulsion further comprises d,α-tocopherol and EDTA.

26) The fluorocarbon emulsion of paragraph 23 wherein d,α-tocopherol is present in 0.0025 w/v or less and EDTA is present in the amount of 0.02 w/v.

27) Use of a perfluorooctyl bromide and perfluorodecyl bromide in the manufacture of a medicament for delivering oxygen to a patient wherein the perfluorooctyl bromide and perfluorodecyl bromide form a discontinuous phase in an aqueous continuous phase to form an emulsion, wherein the perfluorooctyl bromide is present in the amount of 57-60% w/v of the total amount of emulsion and the perfluorodecyl bromide is present in the amount of 1-3% w/v of the total amount of emulsion, further comprising an emulsifying agent.

28) The use of paragraph 27 further comprising egg yolk phospholipid as the emulsifying agent.

29) The use of paragraphs 27 and 28 further comprising NaCl, $NaH_2PO_4.H_2O$, $NaHPO_4.7H_2O$.

30) The use of paragraphs 27-29 wherein the wherein the perfluorooctyl bromide is present in the amount of 58-59% w/v of the total amount of emulsion and the perfluorodecyl bromide is present in the amount of 1-3% w/v of the total amount of emulsion.

31) The use of paragraphs 27 and 28 wherein the perfluorooctyl bromide is present in the amount of 58% w/v of the total emulsion and the perfluorodecyl bromide is present in the amount of 2% w/v of the total amount of the emulsion.

32) Use of a perfluorooctyl bromide and perfluorodecyl bromide in the manufacture of a medicament for delivering oxygen in vivo to a patient wherein the perfluorooctyl bromide and perfluorodecyl bromide form a discontinuous phase in an aqueous continuous phase to form an emulsion, wherein the perfluorooctyl bromide is present in the amount of 58% w/v of the total amount of emulsion and the perfluorodecyl bromide is present in the amount of 2% w/v of the total amount of emulsion, further comprising an emulsifying agent comprising egg yolk phospholipid in the amount of 3.6% w/v of total emulsion.

33) The use of claim 32 further comprising NaCl, $NaH_2PO_4.H_2O$, and $NaHPO_4.7H_2O$.

34) A method of manufacturing a fluorocarbon emulsion for in vivo oxygen transport comprising perfluorooctyl bromide and perfluorodecyl bromide having size stability characteristics for an extended period of time comprising the steps of:

a) preparing an aqueous solution of sodium salts to hot water in a first tank and sparging with nitrogen;
b) adding perfluorooctyl bromide and perfluorodecyl bromide to a second tank and sparging with nitrogen;
c) adding the emulsifying agent to a third tank and adding the contents of the first tank to the third tank;
d) adding the perfluorooctyl bromide and perfluorodecyl bromide to the third tank and mixing the contents to emulsify the perfluorooctyl bromide and perfluorodecyl bromide;
e) directing the contents of the third tank to one or more homogenizer tanks.

35) The method of manufacturing of paragraph 34 wherein the aqueous solution in the first tank is prepared in the temperature range of 65° to 80° C.

36) The method of manufacturing of paragraphs 34 and 35 wherein the aqueous solution is temperature adjusted to 55° to 65° C. during nitrogen sparging.

37) The method of manufacturing of paragraphs 34-36 wherein the sodium salts added to the first tank include sodium phosphate monobasic monohydrate, sodium chloride and edentate calcium disodium.

38) The method of manufacturing of paragraph 34 wherein the perfluorooctyl bromide and perfluorodecyl bromide are maintained in the second tank at 15-25° C.

39) The method of manufacturing of paragraphs 37 and 38 wherein the perfluoroctyl bromide and perfluorodecyl bromide (fluorocarbon solution) are held under vacuum during the nitrogen sparging.

40) The method of paragraph 34 wherein the emulsifying agent is egg yolk phospholipid.

41) The method of paragraph 34 wherein d-α-tocopherol is added to the third tank along with the emulsifying agent.

42) The method of paragraph 34 wherein the d-α-tocopherol is added to the third tank along with the egg yolk phospholipid.

43) The method of paragraphs 34-40 wherein the contents of the first tank are added to the third tank through an in-line filter housing and recirculated through a dispersing mixer.

44) The method of paragraph 43 wherein the in-line filter housing has a mesh of approximately 0.45 μm.

45) The method of paragraphs 43-44 wherein after the contents of the first tank are added to the third tank, the contents are mixed with an agitator.

46) The method of paragraphs 34 and 43-44, the fluorocarbon solution is added to the into the head of the dispersing mixer while the contents of the first tank is recirculating.

47) The method of paragraph 46 wherein the fluorocarbon solution is not added to the dispersing mixer until flow is at least 150 L min.

48) The method of paragraphs 40-42 wherein the contents of the first tank are added to the third tank under a high speed, high-shear mixer to emulsify the fluorocarbon solution.

49) The method of paragraph 48 wherein after the fluorocarbon solution is emulsified, the mixture is recirculated through the dispersing mixer.

50) The method of paragraph 49 wherein the mixture is recirculated at approximately 1600-1750 L mass flow at 240-300 L/min.

51) The method of paragraph 34 wherein the contents of the third tank are directed to the homogenizer tanks through an in-line filter.

52) A fluorocarbon emulsion for use in in vivo oxygenation in humans and other mammals comprising of a continuous aqueous phase and a discontinuous fluorocarbon phase, wherein the discontinuous fluorocarbon phase consists of 58% w/v perfluorooctyl bromide and 2% w/v perfluorodecyl bromide, further comprising an emulsifying agent consisting of egg yolk phospholipid.

53) A fluorocarbon emulsion for use in vivo oxygenation in humans and avoidance of exposure to allogeneic or homologous blood comprising of a continuous phase and a discontinuous fluorocarbon phase with approximately 95-96% w/w of perfluorooctyl bromide and approximately 3-4% w/w of perfluorodecyl bromide, further comprising of an emulsifying agent consisting of egg yolk phospholipid.

54) A fluorocarbon emulsion for oxygen transport to the tissues in humans and other mammals and avoidance of exposure to allogeneic or homologous blood, comprising: a continuous aqueous phase and a discontinuous fluorocarbon phase, wherein the discontinuous fluorocarbon phase consists of perfluorooctyl bromide and perfluorodecyl bromide, wherein the perfluorooctyl bromide is present in the fluorocarbon emulsion at approximately 57-60% w/v of the total emulsion and the perfluorodecyl bromide is present in the emulsion at approximately 1-3% w/v of the total emulsion.

55) The fluorocarbon emulsion of paragraph 54 further comprising an emulsifying agent consisting of egg yolk phospholipid present in the amount of approximately 3.5%-4% w/v.

56) The fluorocarbon emulsion of paragraphs 54 and 55 wherein the emulsion is stabilized by a surfactant selected from the group consisting of fluorinated surfactants and lecithin based surfactants.

57) The fluorocarbon emulsion of paragraph 54 wherein the discontinuous phase consists of approximately 58-59% w/v PFOB and approximately 2-3% w/v PFDB.

58) The fluorocarbon emulsion of paragraph 54 wherein the discontinuous phase consists of approximately 58% w/v PFOB and 2% w/v PFDB.

59) The fluorocarbon emulsion of paragraph 54 wherein upon formation of the emulsion, fluorocarbon particles of a median particle diameter of 0.18 μm or less are formed.

DETAILED DESCRIPTION OF THE PREFERRED EMBODIMENTS

Figure 1:
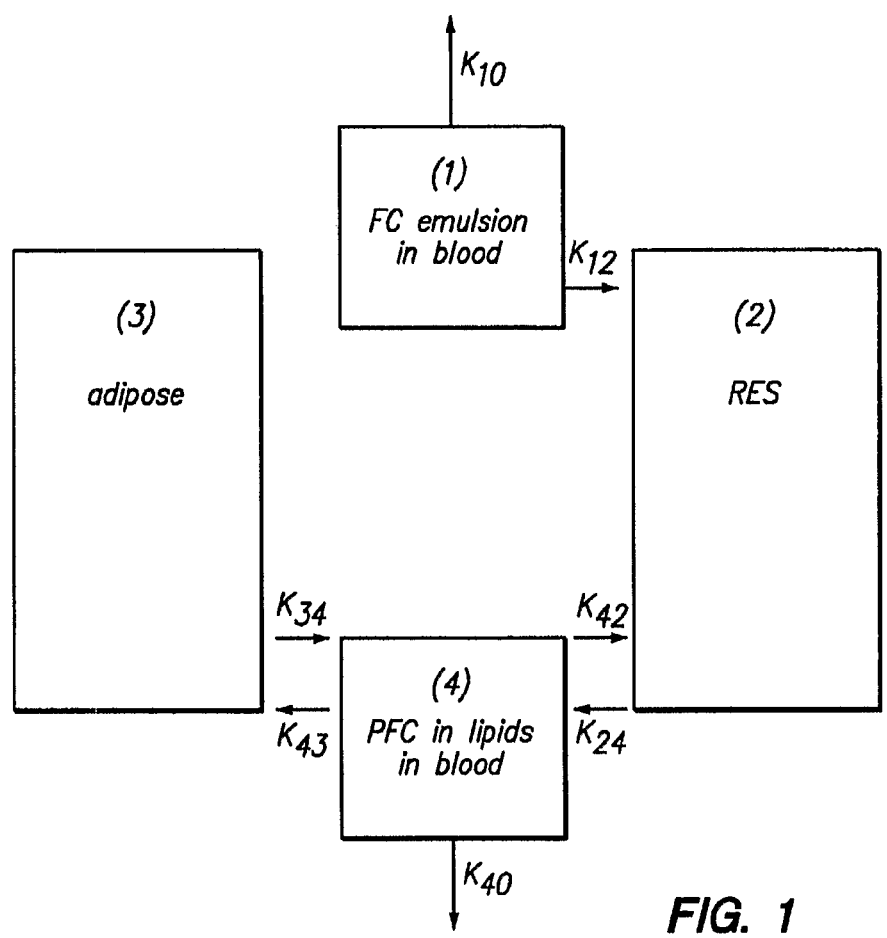
FIG. 1 is a four component pharmacokinetic model for excretion of intravenously administered fluorocarbons.
Figure 2:
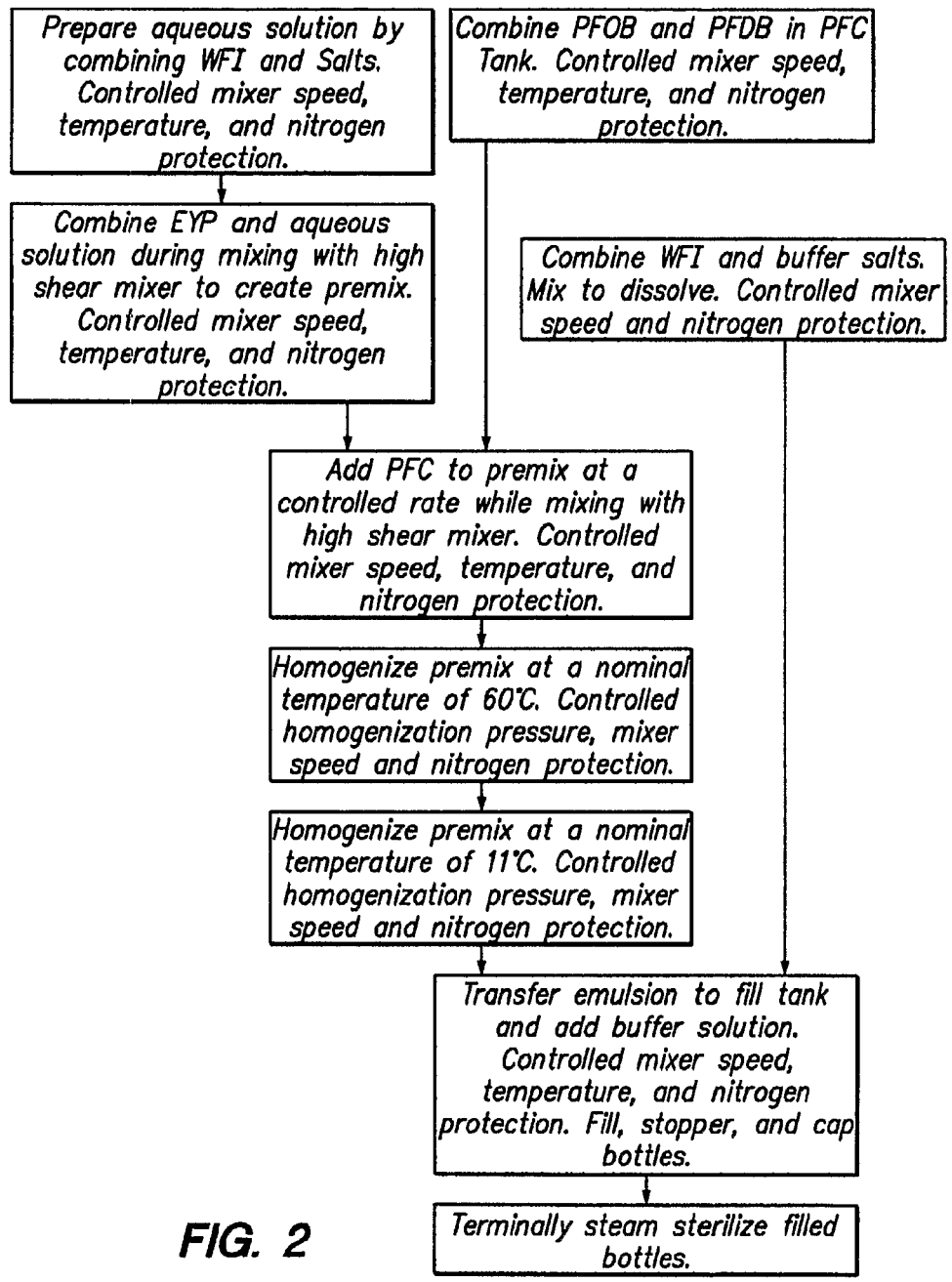
FIG. 2 is a flow chart showing the method steps of making the emulsion according to one embodiment in the present application.

The fluorocarbon emulsions of the present invention comprise two phases: a continuous aqueous phase and a discontinuous fluorocarbon phase. Osmotic agents, buffers and chelators may be included in the continuous phase to maintain osmolarity and pH to promote physiological acceptability. Emulsifying agents are used to aid in the formation and stability of fluorocarbon droplets in the discontinuous phase by forming a layer at the interface between the discontinuous and continuous phase. The emulsifying agent may be comprised of a single compound or multiple compounds such as in the case of multiple surfactants.

As used herein, the expression "weight per volume" or "w/v" will mean grams per 100 cubic centimeters or milliliters of emulsion volume. The expression "weight per weight" will be used and understood to mean the weight fraction(s) of various components that add up to given weight.

The present invention is directed to a fluorocarbon emulsion comprising a mixture of fluorocarbons which is highly stable with excellent biocompatibility and efficacy. The present invention provides for a fluorocarbon emulsion wherein the discontinuous phase is formed by a mixture of PFOB and PFDB. In contrast to prior art emulsions, the fluorocarbon emulsion of the present invention exhibits minimal particle growth upon storage and uses a minimal amount of PFDB to prevent particle growth and avoids the problems of significant organ retention and prolonged half life.

The emulsions of the present invention can be manufactured according to the following procedure. The aqueous solution is prepared by adding pre-weighed quantities of sodium phosphate monobasic monohydrate USP, sodium chloride USP, and edetate calcium disodium to the required quantity of hot water for injection (WFI) at 65 to 80° C. in the aqueous tank (Tank #1). The aqueous solution is nitrogen sparged and temperature adjusted to 55 to 65° C. (+/−5° C.). The required quantities of PFC components (PFOB and PFDB) are added to the PFC tank and maintained at 20+/−5°. The PFC liquid is then sparged with nitrogen to displace dissolved oxygen and then held under vacuum to degas the liquid. After degassing, the PFC liquid is heated under vacuum to 60° C. (+/−5° C.).

The required quantities of egg yolk phospholipid and d-α-tocopherol USP are added to a pre-mix tank (Tank #2) and is purged with nitrogen. Under nitrogen pressure, the aqueous solution of Tank #1 is transferred through an in-line 0.45-μm filter housing to the pre-mix tank (Tank #2) and then recirculated through a dispersing mixer. The contents of the pre-mix tank are mixed with an agitator. After flow is established at not less than 150 L/min, the PFC solution is added into the head of the dispersing mixer while the aqueous solution is recirculating. The PFC is emulsified by adding the PFC to the surfactant (EYP) and aqueous salts dispersion while employing a high-speed, high-shear mixer. This results in optimum surfactant coating of the PFC particles. Nitrogen purging in the tank is continued during pre-mixing. After the PFC has been added and emulsified in the aqueous phase, the mixture is recirculated through the dispersing mixer for 1670+/−70 L mass flow at 280+/−20 L/min.

Following completion of pre-mixing, the emulsion prepared above is circulated from Tank #2 through an in-line 10 μm filter into two homogenizer tanks H1 and H2, to a heat exchanger, and back to Tank #2 at 60+/−5° C. for a total mass flow of 1170+/−5-kg. Homogenization is then conducted first at 60+/−3° C. and then at 11+/−3° C. at controlled pressure to achieve optimum homogenization. In the final step of homogenization, the emulsion is transferred through the homogenizers to Tank #3 instead of returning to Tank #2. This final step of homogenization is described as a "discrete pass" and ensures that all product transferred to the filling tank has been passed through homogenizers.

A nitrogen-sparred buffer solution of sodium phosphate dibasic heptahydrate USP, sodium phosphate monobasic monohydrate USP and sodium chloride USP, in WFI is prepared in Tank #1 (11+/−5° C.) and is transferred to Tank #3 containing the homogenized emulsion through a 0.45 μm filter. The emulsion is agitated for at least 5 minutes prior to circulation through the fill loop at a flow rate of 10+/−1 L/min. The filling temperature is controlled at 11+/−3° C. The emulsion is either passed through a 10 μm filter housing immediately prior to filling or recirculates back to Tank #3. The emulsion is filled into 100-mL bottles (USP Type I glass) and stoppered with 28-mm prewashed, presiliconized grey butyl rubber stoppers under a laminar flow (Class 100) hood. Prior to receiving the stopper the headspace of each bottle is purged with nitrogen. 28-mm aluminum lacquered three-piece overseals are placed on stoppered bottles and manually crimped.

The product is then terminally steam sterilized in a steam overpressure autoclave through the injection of a clean air/clean steam mixture, inspected, and after sterilization, stored at 2 to 8° C. Samples selected from the beginning and end of the filling process are analyzed for conformance to final product specifications.

Example I

Preparation of a 90% w/v PFOB Emulsion with 4% w/v EYP (90/4% w/v)

A reference emulsion containing 90 g PFOB, 4 g egg yolk phospholipid (EYP), and physiological levels of salts and buffers was prepared by high pressure homogenization according to the method of Long (U.S. Pat. No. 4,987,154 which is hereby incorporated by reference in its entirety) to obtain a 90% w/v PFOB emulsion. A secondary fluorocarbon, perfluorodecylbromide (PFDB), was then added to the 90% w/v PFOB emulsion in amounts containing 1%, 2%, 5%, and 10% (w/w) perfluorodecyl bromide to create one PFOB and four PFOB/PFDB emulsions. The four PFOB/PFDB emulsions prepared by the procedure of Example I were placed on accelerated stability testing at 40° C. for three months with a particle size analyzer.

Figure 3:
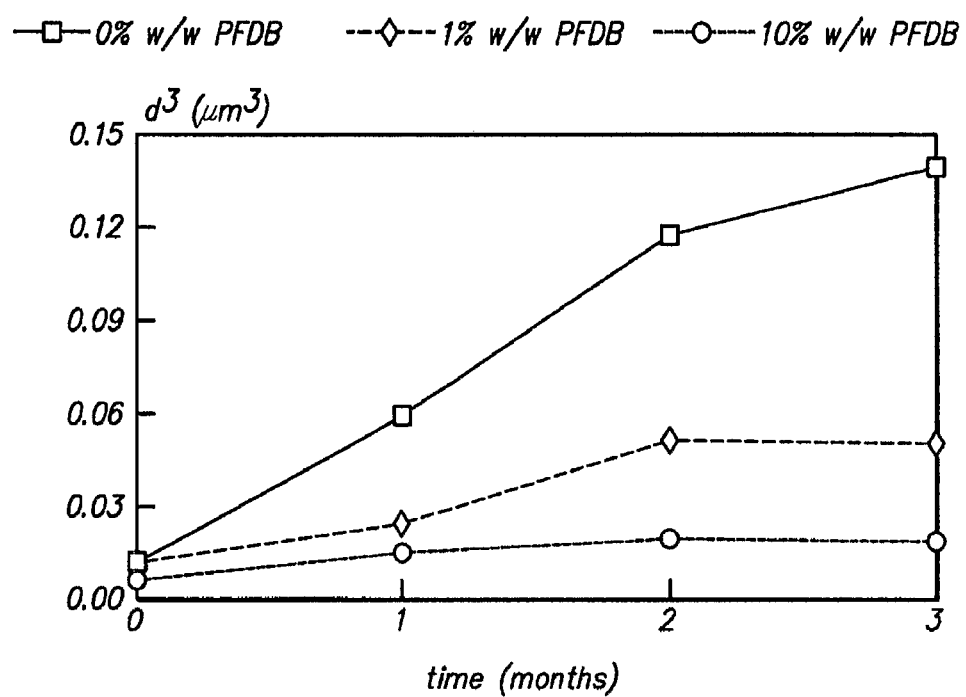
FIG. 3 illustrates a Lifshitz-Slezov-Wagner graph of $d^3$ as a function of time for the 90% w/v PFOB, the 90% w/v PFOB/1% w/v PFDB and the 90% w/v PFOB/10% w/v PFDB emulsions.

Table I demonstrates particle size stability over time, tested with a particle size analyzer, for the one PFOB and four PFOB/PFDB fluorocarbon emulsions. Such emulsions include a control, in which 100% of the fluorocarbon phase is perfluorooctyl bromide, and emulsions of the present invention in which the fluorocarbon phase is 90% to 99% w/w perfluorooctyl bromide, with from 1% to 10% w/w of perfluorodecyl bromide added as a stabilizer. In Table I, "EYP" refers to egg yolk phospholipid, "perflubron" is perfluorooctyl bromide, "PFDB" is perfluorodecyl bromide, and "S" is the rate of particle growth in units of $\mu m^3$/mo. FIG. 3 illustrates typical Lifshitz-Slezov-Wagner graphs of $d^3$ as a function of time for three of the emulsions, the 90% w/v PFOB emulsion, the 90% w/v PFOB/1% w/v PFDB emulsion and the 90% w/v PFOB/10% w/v PFDB emulsion. The cubed term is chosen for the ordinate since the Lifshits-Slezov-Wagner theory predicts that plots of $d^3$ vs time will yield a straight line. In fact, this linear dependence is generally observed for fluorocarbon emulsions.

TABLE I

Stabilizing Effect of Perfluorodecyl bromide on 90% w/v PFOB Emulsion Containing Added Perfluorodecyl bromide with 4% EYP, T = 40° C.)

| PFDB % w/w | Initial Size (μm) | Size After One Month | Size After Two Months | Size After Three Months | S × 1000 |
|---|---|---|---|---|---|
| 0% | 0.23 (0.13) | 0.39 (0.19) | 0.49 (0.20) | 0.52 (0.23) | 44.4 |
| 1% | 0.23 (0.12) | 0.29 (0.16) | 0.37 (0.19) | 0.37 (0.18) | 14.2 |
| 2% | 0.19 (0.09) | 0.23 (0.12) | 0.26 (0.14) | 0.32 (0.17) | 8.3 |
| 5% | 0.18 (0.08) | 0.20 (0.10) | 0.24 (0.13) | 0.28 (0.14) | 5.4 |
| 10% | 0.20 (0.12) | 0.25 (0.13) | 0.27 (0.14) | 0.27 (0.16) | 3.9 |

(parentheses indicate the standard deviation in the distribution of particle sizes)

The above results demonstrate that higher concentrations of PFDB stabilize 90% w/v PFOB emulsions more effectively than lower concentrations of PFDB. The 90% w/v PFOB/10% w/w PFDB fluorocarbon emulsion proved to be the most stable with the smallest particle size over a three month period.

Example II

Stabilization of a 60% w/v PFOB Emulsion

Perfluoroctyl Bromide/Perfluorodecyl Bromide

An emulsion was prepared according to the procedure of Long (U.S. Pat. No. 4,987,154) and the teachings of Example I, but instead of a 90% w/v PFOB emulsion, a 60% w/v PFOB emulsion was made and a second 60% w/v PFOB emulsion stabilized with 10% w/v PFDB. Table II compares particle size increase on accelerated stability testing at 40° C. for a period of three months for a 60% w/v perflubron emulsion containing no PFDB to a 60% w/v perflubron emulsion containing 10% w/v PFDB. The stability testing was done with a particle size analyzer. Table II shows the reduction of particle growth over a three month period for the 60% w/v PFOB emulsion with 10% w/v PFDB added.

TABLE II

Stabilization of a 60% w/v Fluorocarbon Emulsion
(Perfluoroctyl Bromide/Perfluorodecyl Bromide)

| Sample | Initial Size (μm) | Size after 1 month (40° C.) | Size after 2 months (40° C.) | Size after 3 months (40° C.) | S × 1000 (μm³/mo) |
|---|---|---|---|---|---|
| 0% w/v PFDB | 0.20 | 0.34 | 0.38 | 0.39 | 16.9 |
| 10% w/v PFDB | 0.18 | 0.20 | 0.23 | 0.23 | 2.3 |

The results demonstrate a significant reduction of particle growth over a three month period for the 60% w/v PFOB emulsion with 10% w/v PFDB added in comparison to the 60% w/v PFOB emulsion.

Example III

Differences in Intravascular Persistence for Fluorocarbons in Two-Component Disperse Phase Emulsions (60% PFOB w/v/30% PFDB w/v)

Figure 4:
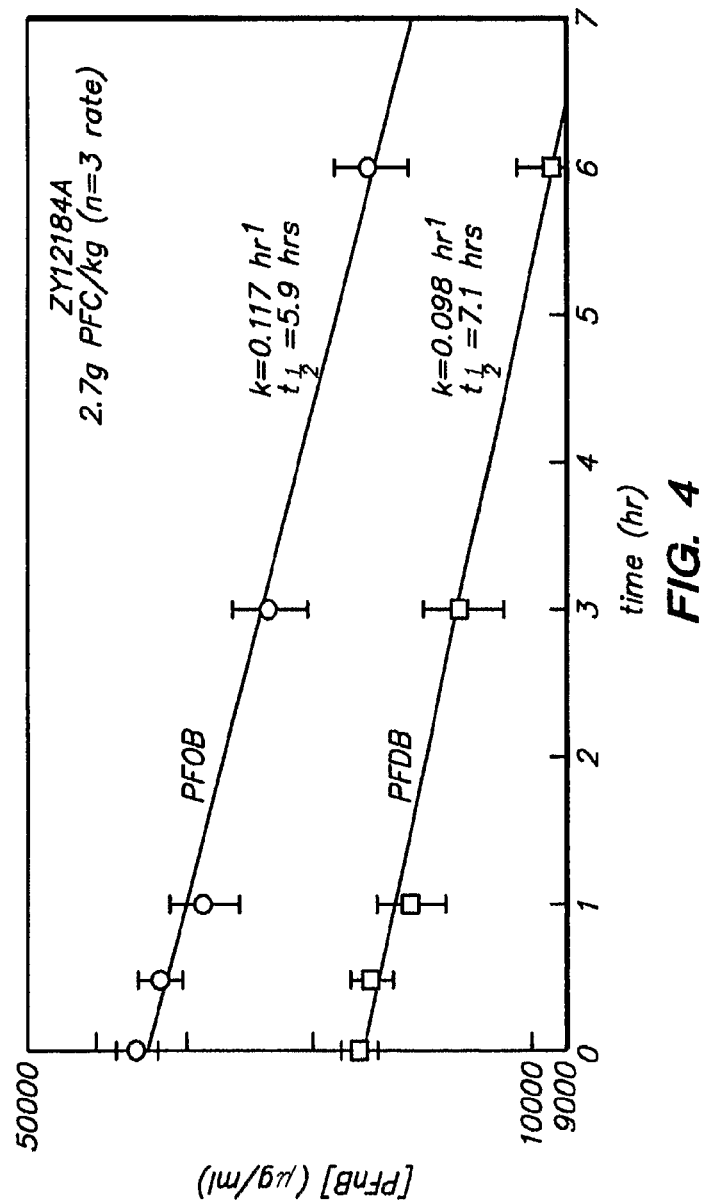
FIG. 4 shows intravascular persistence of PFOB and PFDB in rats following intravenous administration of a 60/30% w/v PFOB/PFDB fluorocarbon emulsion and 6% EYP (2.7 g PFC/kg)

FIG. 4 represents typical data for the removal of both PFOB and PFDB. FIG. 4 shows a plot of SdFFF fractogram obtained for a 60/30 (% w/v) ratio of PFOB/PFDB stabilized by 6% w/v EYP for the intravascular persistence of PFOB and PFDB in rats. In general, the rate constant for PFDB removal is 20-30% less than that of PFOB.

The emulsion composition with the data shown in FIG. 4 contains a 60/30% (w/v) ratio of PFOB/PFDB stabilized by 6% w/v EYP. In this case, the rate constant for PFDB removal is 20% higher than that of PFOB. It might be assumed that in the first few hours after administration that the removal from blood is controlled by k12 (see FIG. 1). The fluorochemical composition of circulating emulsion droplets should, therefore, remain intact. How is it then that the two disperse phase components could have different rate constants? To answer this question, the composition of the intravenously administered droplets can be examined through the use of sedimentation field-flow fractionation (SdFFF) coupled with gas chromatography, thereby confirming the nature of the droplets.

Figure 5:
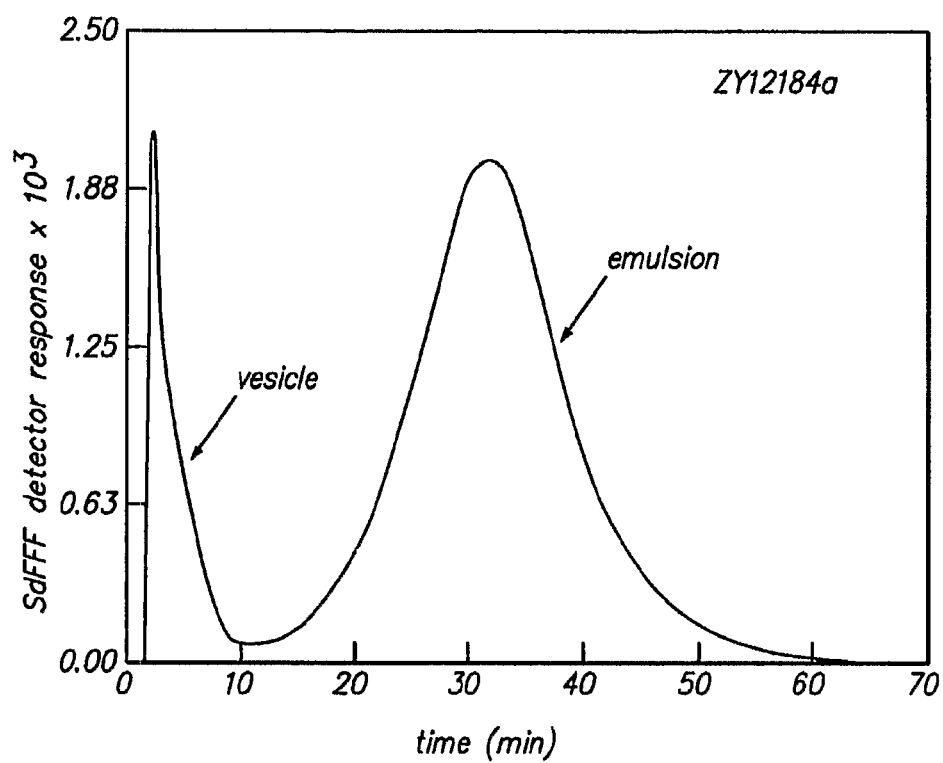
FIG. 5 shows an SdFFF fractogram obtained for a PFOB/PFDB emulsion showing a fraction of phospholipid vesicles close to the void and a fraction of the emulsion droplets stabilized by a monomolecular layer of phospholipid at ca. 0.15 μm.

FIG. 5 shows a plot of the SdFFF factogram obtained for 60/30% w/v ratio of PFOB/PFDB stabilized by 6% w/v EYP. The data are presented as mass weighted detector response vs. droplet diameter. The shoulder which appears next to the sharp void volume peak is due to the presence of phospholipid vesicles which contain only small amounts of solubilized fluorochemical. The larger sized (later eluting) peak is attributable to fluorochemical emulsion droplets which are stabilized by an interfacially adsorbed monolayer of phospholipid. The concentration in this type of droplet has been confirmed in monodisperse fractions by gas chromatography.

Example IV

Partitioning of Disperse Phase of Components in a 60/30% w/v PFOB/PFDB Emulsion

Figure 6:
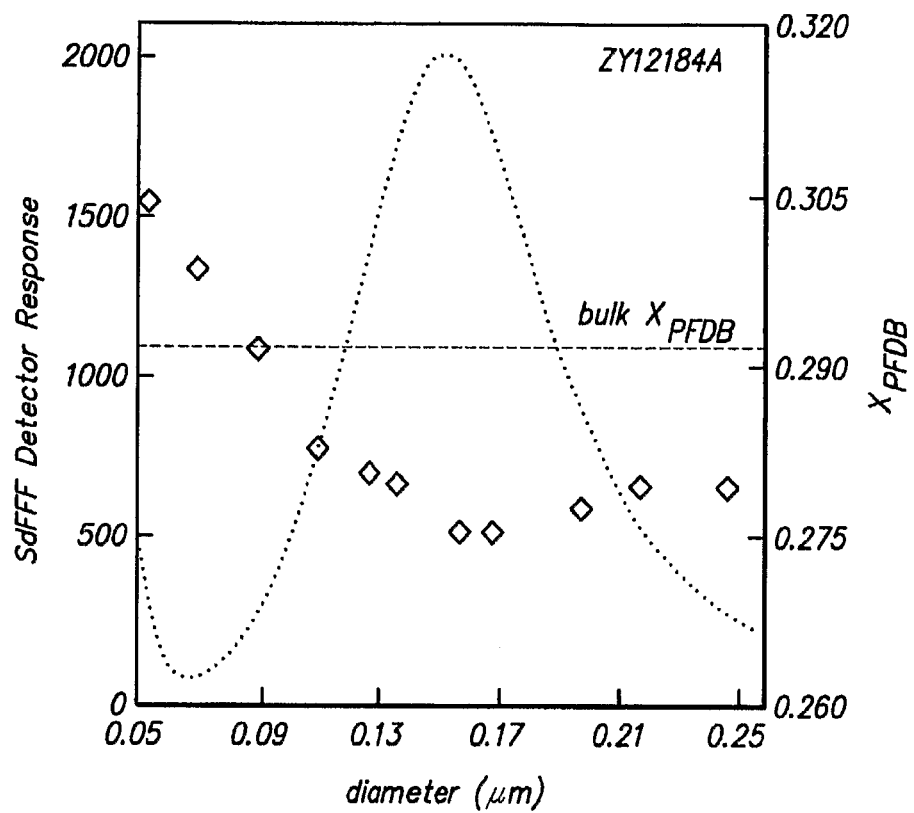
FIG. 6 shows an SdFFF study illustrating the partitioning which occurs as a function of droplet size. The right axis (given by circles in the plot) represents the mole fraction of PFDB in monosized droplet fractions as determined by gas chromatography. PFOB and PFDB are found to be enriched in the large and small drops respectively.

FIG. 6 illustrates the partitioning of the disperse phase components which occurs between various monosized droplets fractions in a 60/30% w/v ratio of PFOB/PFDB stabilized by 6% EYP. Shown in FIG. 6 is the SdFFF fractogram (plotted on the left axis) and the mole fraction of PFDB in different monosized droplets as determined by gas chromatography (bulk $X_{pfdb}$=0.291). The bulk composition is the composition expected across the entire particle size distribution in a coalescence mediated process, since no partitioning of components can occur by this mechanism. No scattering correction has been applied to this data. Thus, the distribution tends to overweight the larger droplets which scatter light strongly. This leads to a shift of distribution to larger median diameters. Although the median diameter is 0.15 μm, the maximum fluorochemical content in the droplets is observed at ca. 0.13 μm. The two composition points to the far left (at small sizes) appear to be outside of the particle size distribution yet contain ca. 10% and 20% of the peak fluorochemical concentration (i.e. they are clearly on the tail of the distribution).

It is clear that these smaller droplets are significantly enriched in the slower diffusing PFDB component (by 5% or more), while the larger droplets are enriched by up to 5% in PFOB. The degree of partitioning is less than was observed for PFOB/PFDB emulsions which contain only 10% w/w PFDB. This is expected since the emulsions are predicted to be more stable to Ostwald ripening as the concentration of secondary fluorochemical is increased.

Example V

Figure 7:
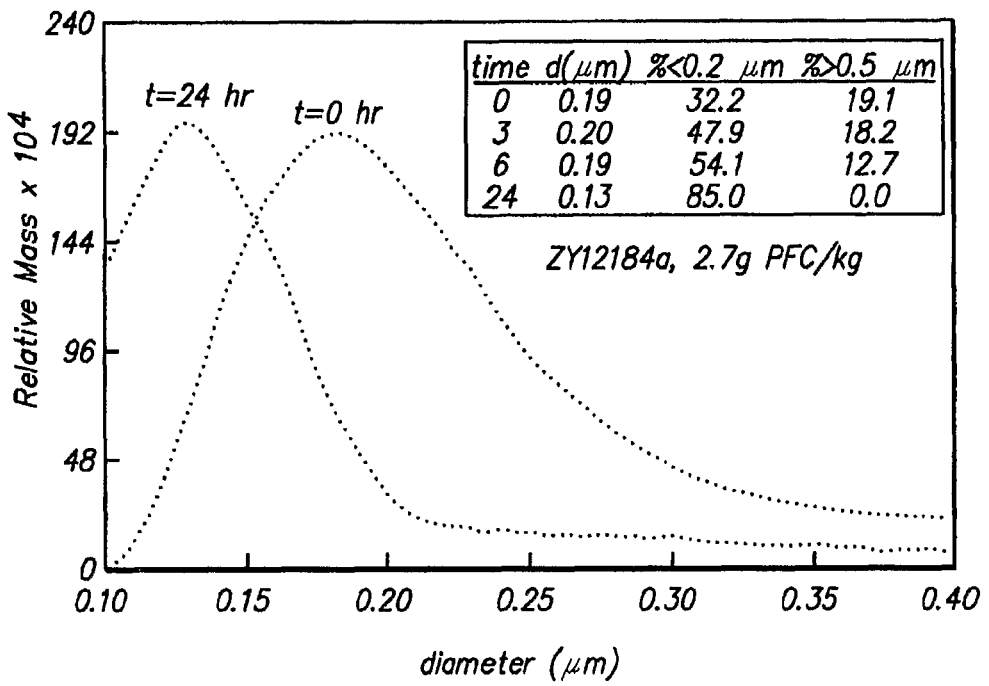
FIG. 7 shows particle size distributions of the emulsion of Example V in ex-vivo rat blood immediately following intravenous administration of a 2.7 g PFC/kg dose after 24 hr. The inset shows changes in the particle size distribution over time. Once in the vascular compartment, the larger droplets are selectively removed by the reticuloendothelial system.

SdFFF Studies of Changes in the Particle Size Distribution on Fluorochemical Emulsions in Ex-Vivo Blood FIG. 7 is a plot of the particle size distributions observed in ex vivo rat blood following intravenous administration of a 60/30% (w/v) ratio of PFOB/PFDB stabilized by 6% w/v EYP at a dose of 2.7 g PFC/kg. There is a slight increase in droplet size for the ex vivo emulsion immediately after injection relative to the control (0.19 μm vs. 0.15 μm). This may reflect some degree of opsonization by serum proteins, increased droplet flocculation, or alternatively the interference of some particles in the plasma which have particle sizes in the range from 0.15 μm to 1 μm. After 24 hr., a significant fraction of the large droplets have been preferentially removed. The inset in FIG. 7 shows that little change is noted in the mode diameter at initial times. However, significant increases in the population of droplets less than 0.2 μm are noted even after 3 and 6 hr. As well, a decrease in the proportion of droplets greater then 0.5 μm is noted.

Figure 8:
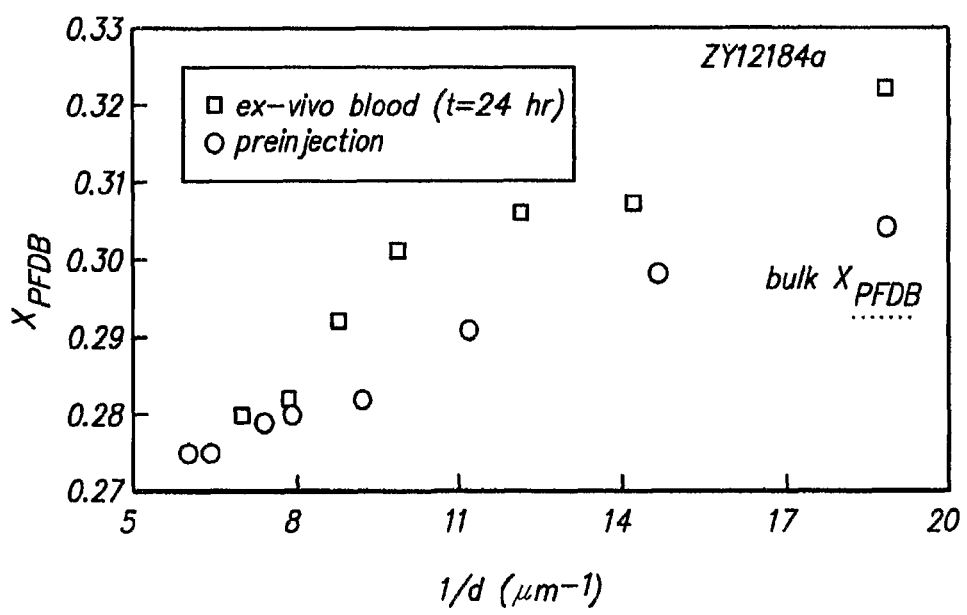
FIG. 8 is a plot of the mole fraction of PFDB in monosized emulsion droplets obtained from ex-vivo rat blood vs. 1/d, following intravenous administration of 2.7 g PFC/kg of a 60/30% w/v PFOB/PFDB, 6% EYP emulsion. Data plotted includes the emulsion prior to injection, and the sample after 24 hr. The mole fraction of the less soluble fluorochemical component, PFDB, increases after administration.

All of these results taken together indicate that macrophages selectively remove the larger particles from the distribution. Since the smaller particles are more concentrated in PFDB it is expected that the concentration of PFDB-rich particles will increase over time. FIG. 8 shows a plot of the $X_{pfdb}$ vs. 1/d for the 24 hr sample relative to the control (i.e. prior to injection). These points are obtained as before, by collecting monosized fractions across the droplet distribution and analyzing by gas chromatography for fluorochemical content. The $X_{pfdb}$ is increased for the ex-vivo sample relative to the control indicating that the circulating droplets are indeed enriched in the PFDB component, by as much as 12%. This is significantly increased over the 5% values observed in the control.

sion-particle-induced stimulation of phagocytic cells by larger fluorocarbon particles created by higher amounts of fluorocarbons in the more concentrated emulsions.

TABLE III

Stabilization of a Fluorocarbon Emulsions with PFDB (Perfluoroctyl Bromide/Perfluorodecyl Bromide)

| Sample | Initial Size (μm) | Size after 1 month (40° C.) | Size after 2 months (40° C.) | Size after 3 months (40° C.) | S × 1000 (μm³/mo) |
|---|---|---|---|---|---|
| 58% w/v PFOB/2% w/v PFDB* | 0.18 | 0.19 | N.A. | 0.21 | 0.80 |
| 60% w/v PFOB | 0.20 | 0.34 | 0.38 | 0.39 | 16.9 |
| 60% w/v PFOB/10% w/v PFDB | 0.18 | 0.20 | 0.23 | 0.23 | 2.3 |
| 90% w/v PFOB | 0.23 | 0.39 | 0.49 | 0.52 | 44.4 |
| 90% w/v PFOB with 10% w/v PFDB | 0.20 | 0.25 | 0.27 | 0.27 | 3.9 |
| 90% w/v PFOB with 1% w/v PFDB | 0.23 | 0.29 | N.A. | N.A. | N.A. |

*Data from GMP lot where particle size (in all cases, from a particle size analyzer Horiba CAPA-700) was measured on a 1, 3, 6 month scale per ICH guidelines. The 6$^{th}$ month particle size of the 58%/2% w/v PFOB/PFDB emulsion was 0.22 μm.

Example VI

A PFOB/PFDB fluorocarbon emulsion is made according to the teachings of the present application to formulate a 58% w/v PFOB and 2% w/v PFDB fluorocarbon discontinuous phase in a continuous aqueous phase. Its components are:

| | |
|---|---|
| C8F17Br (PFOB) | 58% w/v |
| C10F21Br (PFDB) | 2% w/v |
| Egg Yolk Phospholipid | 3.6% w/v |
| d, α - tocopherol | 1.0018% w/v |
| NaCl | 0.36% w/v |
| NaH2PO4•H2O | 0.069% w/v |
| Na2HPO4•7H2O | 0.474% w/v |
| EDTA | 0.02% w/v |

This 58%/2% w/v PFOB/PFDB emulsion has an osmolality of 300 to 310 mOsm/kg, a pH of 7.0 to 7.2 and a viscosity of approximately 4 cPoise (at a shear of 1/sec).

The emulsion made according to Ex. VI proved as stable or more stable as other emulsions such as 60/10% w/v PFOB/PFDB emulsions or approximately as stable as 90/10% w/v PFOB/PFDB emulsions but without the negative side effects of that emulsion. By using 500% less PFDB than the 60/10% w/v PFOB/PFDB emulsion, the emulsion of Ex. VI avoids excess PFDB with its longer half life and organ retention problems. In comparison to the 90/10% w/v PFOB/PFDB emulsion, the emulsion of Example VI uses almost 50% less PFOB and 500% less PFDB yet proves as efficacious in oxygen delivery (see later Examples) as the 90/10% w/v emulsion. The side effects of the emulsion of Example VI, such as flu like side effects attributed to large fluorocarbon particles, were much less pronounced in comparison to the 90/10% w/v PFOB/PFDB emulsion. The results of nonclinical studies demonstrated that the flu-like side effects are due to short-lived release of cytokines, prostaglandins, thromboxane, and/or endoperoxide products, in response to the emulsion.

The results in Table III demonstrate the emulsion of Ex. VI has much greater stability over time (S×1000 of 0.80 μm, which is the rate of particle growth in units of μm³/mo) than the other listed emulsions. The 60% w/v PFOB and the 90% w/v PFOB emulsions had very high S values of 16.9 and 44.4 μm respectively. The addition of PFDB to both emulsions proved to help stabilize the emulsions considerably with the 60% w/v PFOB/10% w/v PFDB and the 90% w/v PFOB with 10% w/v PFDB with S values of 2.3 and 3.9 respectively. The S value of 0.80 for the 58% w/v PFOB/2% w/v PFDB of Example VI proved to be significantly improved in comparison to the other emulsions and unexpected.

The emulsion of Example VI should be administered intravenously in an aseptic manner. It is ideally supplied in a 110-mL single use bottle sealed with a spikeable rubber stopper and an aluminum overseal. The emulsion should be stored refrigerated between 2° C.-8° C. and should not be frozen. The emulsion should brought to room temperature prior to administration and should be gently inverted repeatedly (at least 30 times) for approximately 1 minute to ensure complete homogenous appearance of the emulsion. Dosage varies on the individual and its use but is generally 1-3 ml/kg or 1-4 ml/kg.

Example VII

Long Term and Accelerated Testing of the Fluorocarbon Emulsion Made According to the Teachings of Example VI For determining the long term shelf life of the emulsion made according to the teachings of Example VI, stability data was generated at defined time points over a 24-month window with a Horiba CAPA-700 particle size analyzer and statistically analyzed with a commercially available stability software system (SCIENTEK™, Tustin, Calif.). The emulsion was made and then stored in inverted orientation for both long-term conditions (5° C.) for up to 24 months and accelerated storage conditions (25° C.) for up to 6 months. The emulsion made according to Example VI was measured both on accelerated testing (6 months) and long-term test (24 months).

TABLE IV

Emulsion droplet size, results for long-term and accelerated stability of the emulsion of Ex. VI.

| | Initial Size (μm) | 1 | 3 | 6 | 9 | 12 | 18 | 24 |
|---|---|---|---|---|---|---|---|---|
| 58% w/v PFOB/2% w/v PFDB Long-term Testing | 0.16 | * | 0.20 | 0.21 | 0.22 | 0.23 | 0.20 | 0.21 |
| 58% w/v/PFOB/2% PFDB Accelerated Testing | 0.16 | 0.21 | 0.22 | 0.23 | * | * | * | * |

Lots were from a particle size analyzer Horiba CAPA-700

The results demonstrate that the emulsion of Example VI has very stable long term stability up to 24 months. By analyzing data from the SCIENTEK stability software system, which performs statistical regression analysis of data and produces a one-sided 95% confidence predicted expiry date (in accordance with FDA draft guidance in 1998), taking into consideration stability issues such as free fatty acids, appearance, pH, and egg yolk phospholipid content, osmolality and lyso-phosphatidyl choline, an expiry date of 29 months was recommended.

Example VIII

A PFOB/PFDB fluorocarbon emulsion is made according to the teachings of the present invention to formulate a 58% w/v PFOB and 2% w/v PFDB fluorocarbon phase in a continuous aqueous phase. Its components are:

| | |
|---|---|
| C8F17Br (PFOB) | 58% w/v |
| C10F21Br (PFDB) | 2% w/v |
| Egg Yolk Phospholipid | 3.6% w/v |
| NaCl | 0.36% w/v |
| NaH2PO4•H2O | 0.069% w/v |
| Na2HPO4•7H2O | 0.474% w/v |

A variation to the fluorocarbon emulsion of Example VI is made but without d,α-tocopherol and EDTA. This 58%/2% w/v PFOB/PFDB emulsion has an osmolality of 300 to 310 mOsm/kg, a pH of 7.0 to 7.2 and a viscosity of approximately 4 cPoise (at a shear of 1/sec).

Example IX

Pharmacokinetics and Tissue Distribution of Perflubron and Perfluorodecyl Bromide in Rats Following a Single Intravenous Administration of the Emulsion of Ex. VI This study was designed to assess the pharmacokinetics and tissue distribution of PFOB and PFDB following a single intravenous administration of the emulsion of Ex. VI at various time intervals at dose levels of 1.8 and 3.6 g PFC/k in male and female Sprague Daley rats, aged 7-9 weeks, weight between 190-267 grams. For pharmacokinetics, 160 rats were divided into 20 groups (N=4 rats/sex/dose/time interval) and for tissue distribution, 156 rats were divided into 26 groups (n=3 rats/sex/dose/time interval). The time intervals for pharmacokinetics blood sampling were 0.083, 0.5, 1, 3, 6, 12, 36, 48, 72 and 96 hours. The time intervals for tissue sampling was predose, 24 hours, 1, 2, 4, 8, 13, 17, 21, 26, 39, 52 and 72 weeks.

Pharmacokinetics

Following administration, no adverse clinical signs were observed in the rats. Six pharmacokinetic parameters were determined following a single intravenous dose of 1.8 gPFC/kg or 3.6 g PFC/kg in both the male and female rats as shown in the tables below. The average terminal t1/2 of PFOB for male and female rats dosed with 1.8 g PFC/kg was ~73 hours compared to an average terminal t1/2 of 181 hours for animals dosed with 3.6 g PFC/kg. By comparison, the terminal t1/2 was several orders of magnitude greater for PFDB: ~25,130 hours (male, 1.8 g PFC/kg), ~4800 hours (female, 1.8 g PFC/kg), ~12,550 hours (male 3.6 g PFC/kg) and ~7,600 hours (female, 3.6 g PFC/kg).

The volume of distribution (Vd) for PFOB was from ~1200 to 2200 g/kg for both sexes and both doses. In contrast, the range of the volume of distribution for PFDB was from ~1,650,000 to 6,130,000 g/kg for both sexes and both doses. The Vd for PFDB was therefore about three orders of magnitude larger than the Vd for PFOB.

TABLE V

Pharmacokinetic parameters of PFOB in blood of male and female Sprague Dawley rats after a single intravenous administration

| | PFOB (1.8 g PFC/kg) | | PFOB (3.6 g PFC/kg) | |
|---|---|---|---|---|
| Parameter | Male | Female | Male | Female |
| $AUC_{(o-\infty)}$ (mg-h/g) | 122.69 | 126.89 | 566.15 | 541.58 |
| $AUC_{(o-last)}$ (mg-h/g) | 122.65 | 126.86 | 566.13 | 541.55 |
| $T_{1/2}$ (h)* | 68.18 | 78.46 | 237.66 | 123.36 |
| Vd(g/kg)** | 1443.18 | 1605.67 | 2191.83 | 1182.97 |
| $MRT_{(0-last)}$ (h) | 14.67 | 14.19 | 6.39 | 6.65 |
| Cl (g/h/kg) | 6.01 | 5.41 | 8.93 | 6.70 |

*T½ was calculated using the last 3 or 4 data points
**based don the terminal phase

TABLE VI

Pharmacokinetic parameters of PFDB in blood of male and female Sprague Dawley rats after a single intravenous administration

| | PFDB (1.8 g PFC/kg) | | PFDB (3.6 g PFC/kg) | |
|---|---|---|---|---|
| Parameter | Male | Female | Male | Female |
| $AUC_{(o-\infty)}$ (mg-h/g) | 10.65 | 7.54 | 27.62 | 22.87 |
| $AUC_{(o-last)}$ (mg-h/g) | 6.88 | 6.86 | 24.67 | 21.99 |

TABLE VI-continued

Pharmacokinetic parameters of PFDB in blood of male and female
Sprague Dawley rats after a single intravenous administration

| Parameter | PFDB (1.8 g PFC/kg) | | PFDB (3.6 g PFC/kg) | |
| --- | --- | --- | --- | --- |
| | Male | Female | Male | Female |
| $T_{1/2}$ (h)* | 25128.92 | 4796.43 | 12547.3 | 7613.17 |
| Vd(g/kg)** | 6128576 | 1652163 | 2359442 | 1728719 |
| $MRT_{(0-last)}$ (h) | 332.26 | 113.33 | 485.23 | 438.08 |
| Cl (g/h/kg) | 169.05 | 238.76 | 130.34 | 157.39 |

*$T^{1/2}$ was calculated using the last 3 or 4 data points
**based don the terminal phase Tissue Distribution 26 groups (N=3 rats/sex/group). Prior to euthanasia, body weights were recorded. At designated times (see below), rats were anesthetized with METOFANE® and esanguinated via the abdominal artery. Blood was collected into syringes containing EDTA and transferred into sealed plastic containers for storage at approximately −20° C. until analyzed. Resultant data were included in the determination of pharmacokinetic parameters. The following tissues were collected from each rat and placed in sealed containers and stored frozen at −20° C. Prior to freezing, blood and tissue samples were processed for analysis. PFOB and PFDB were quantified in blood and tissues using a GC headspace method validated by Oread. The method was validated in the liver and then cross validated to all other tissues, blood, and serum. The tissues collected and analyzed include heart, lungs, abdominal fat, spleen, liver, mesenteric lymph nodes, kidneys, adrenals, testes, ovaries, uterus, whole brain, eyes, skeletal muscle, femoral bone marrow, and gastrointestinal tract.

The concentration of PFOB and PFDB was determined in the tissues in both sexes at 12 time points. For the males, this was a total of 360 individual results including blood. There were 24 additional results for the female.

In the males, approximately 59% of the PFOB dose was found in the liver at 24 hours for animals receiving a total dose of 1.8 g PFC/kg. The percent of total dose was <1% in the spleen. This increased to approximately 69% in males dosed with 3.6 g PFC/kg. In the females, approximately 4% of the PFOB dose was found at 24 hours in the spleen and approximately 63% of the PFOB dose was found at 24 hours in the liver for animals receiving a total dose of 1.8 gPFC/kg. In the females receiving 3.6 g PFC/kg, the percent total dose was found to be approximately 53% in the liver and <1% in the spleen.

In the male rats, approximately 15% and 85% of the total dose of PFDB (1.8 g PFC/kg) was found in the spleen and liver, respectively. The percent of total dose of PFDB found in the spleen and liver was approximately 11% and 69%, respectively, in the males that received 3.6 g PFC/kg. In the females, the percentage of PFDB was found to be approximately 14% and 86% of the total dose of PFDB in the spleen and liver, respectively. When the total dose of PFC was increased to 3.6 g/kg, the spleen contained approximately 8% and the liver contained approximately 62% of the total dose.

The absolute concentration of PFOB at 24 hours was above 100 µg/g in all tissues except the eyes and skeletal muscles in males dosed with 1.8 g/kg of PFC. For males dosed with 3.6 PFC/kg, the concentration of PFOB was above 100 µg/g in all tissues. The absolute concentration of PFOB was above the upper limit of quantification in the eyes on average. In females dosed with 1.8 g PFC/kg, the concentration of PFOB was greater than 100 µg/g in all tissues except the blood, eyes, and skeletal muscle. The concentration of PFOB was greater than 100 µg/g at 24 hours in all tissues in females dosed with 3.6 g/kg of PFC. In addition, the concentration was greater than 10 mg/g in the liver and bone marrow for all four groups.

The absolute concentration of PFDB was above 1 µg/g in all tissues for both sexes and both doses at 24 hr. The concentration of PFDB was greater than 1 mg/g at 24 hours in the spleen and liver of males dosed with 1.8 g PFC/kg. The concentration of PFDB was greater than 1 mg/g in the spleen, liver, and bone marrow of males dosed with 3.6 PFC/kg. The females in the 3.6 g PFC/kg dose group had PFDB concentrations above 1 mg/g in the lymph nodes, spleen, liver and bone marrow.

Both the pharmacokinetics and the tissue distribution studies clearly demonstrate the desirability of limiting the amount of PFDB in administered PFOB/PFDB emulsions due to the much longer t1/2 life of PFDB in comparison to PFOB and its retention in various tissues and organs. Thus any PFOB/PFDB emulsion should be formulated to avoid excess amounts of PFDB than is absolutely necessary.

Example X

Pharmacokinetics of the PFOB/PFDB Emulsion of Example VI in Healthy Human Volunteers Two randomised, controlled, double-blind, parallel group, Phase 1 studies were conducted in healthy human patients with the fluorocarbon emulsion made according to Example VI. Blood and expired air samples were analysed for PFOB and PFDB after a single intravenous dose of 1.2 or 1.8 g PFC/kg of the fluorocarbon emulsion of Example VI in healthy human volunteers to determine pharmacokinetics. Blood samples were collected up to 336 hours post-dosing.

Examination of the PFC blood concentration-time profiles in both studies indicated that the initial peak concentration ($C_{max}$) was independent of the absolute dose (body weight times the respective per-kg dose) for subjects within each per-kg dose group, suggesting that the distribution space for PFCs is a fixed percentage of the body mass (most likely the blood volume). The disposition of PFOB and PFDB were dose-dependent.

There was an initial distribution phase during the first 2-4 hours, followed by a slower initial elimination phase. This initial Michaelis-Menten decline of PFCs in blood was probably due to a saturable RES uptake of PFCs in blood, while the slower terminal elimination phase is an indication of the prolonged persistence of PFCs in body tissue (most likely the adipose tissues).

The mean initial PFOB elimination half-life during the first 12 hours ($t_{1/2,12h}$) was shorter with 1.2 g PFC/kg dose than with 1.8 g PFC/kg dose. The pharmacokinetic parameters for PFOB and PFDB for this Example are shown in Tables VII and VIII.

TABLE VII

Elimination Half-Life Values for PFOB and PFDB

| Parameter | Emulsion Dose | |
|---|---|---|
| | 1.2 g PFC/kg | 1.8 g PFC/kg |
| PFOB | | |
| $C_{max}$ (mg/L) | 13,650 ± 1,610 | 22,688 ± 2,993 |
| AUC (0-336) (mg h/L) | 10,1707 ± 41,732 | 284,837 ± 52,348 |
| $t_{1/2,\,12\,h}$* | 6.55 ± 2.06 | 10.5 ± 2.1 |
| PFDB | | |
| $C_{max}$ (mg/L) | 540 ± 125 | 978 ± 499 |
| AUC (0-336) (mg h/L) | 6,637 ± 3,098 | 16,344 ± 3,191 |
| $t_{1/2,\,12\,h}$* | 13.7 ± 3.6† | 18.7 ± 3.5‡ |

*Initial elimination half-life within the first 12 h post dose.
†N = 3 due to nonreportable values ($r^2$ < 0.95) for 5 subjects.
‡N = 7 due to nonreportable values ($r^2$ < 0.95) for one subject.

TABLE VIII

Elimination Half-Life Values for PFOB and PFDB

| Parameter | Emulsion Dose | |
|---|---|---|
| | 1.2 g PFC/kg | 1.8 g PFC/kg |
| PFOB | | |
| $C_{max}$ (mg/L) | 12,574 ± 1,900 | 21,813 ± 3,728 |
| AUC (0-336) (mg h/L) | 79,200 ± 26,869 | 238,842 ± 75,793 |
| $t_{1/2,\,12\,h}$* | 5.41 ± 1.71† | 7.66 ± 1.02† |
| PFDB | | |
| $C_{max}$ (mg/L) | 670 ± 420 | 884 ± 196 |
| AUC (0-336) (mg h/L) | 4,628 ± 1,949 | 11,161 ± 4,044 |
| $t_{1/2,\,12\,h}$* | 7.35, 13.6‡ | 12.6 ± 4.1‡ |

*Initial elimination half-life within the first 12 h post dose.
†N = 5 due to nonreportable values ($r^2$ < 0.95) for the other 3 subjects.
‡Individual reportable values ($r^2$ < 0.95).

Example XI

Pharmacokinetics of the Fluorocarbon Formulation of Example VI in Human Subjects Undergoing Noncardiac Surgical Procedures The pharmacokinetics of PFOB and PFDB were determined after the administration of the fluorocarbon emulsion of Example VI to subjects undergoing total hip replacement or spinal surgery or a variety of urologic and gynaecologic procedures including radical retropubic prostatectomy, radical hysterectomy, cystectomy and combined procedures. Human subjects in one study received either 0.9 g PFC/kg or 1.8 g PFC/kg of the fluorocarbon formulation of Example VI and those in a second study received 1.8 g PFC/kg of the fluorocarbon formulation of Example VI. The pharmacokinetic parameters for PFOB and PFDB are summarized in Table IX.

Whole blood concentrations of PFOB were approximately 30-fold higher than those of PFDB, consistent with their relative proportions in the administered formulation (58% w/v PFOB: 2% w/v PFDB). Mean values for PFOB and PFDB $C_{max}$ increased in reasonable proportion to the increase in dose. Although the mean values for $AUC_\infty$ at 1.8 g PFC/kg were more than 2-fold greater than those at 0.9 g PFC/kg, the large variability precludes any conclusions of nonlinearity in the pharmacokinetics of either PFOB or PFDB. Mean elimination half-lives ($t_{1/2}$) for both compounds ranged from ~2.4 hours to ~5.6 hours. These values are lower than values obtained in healthy volunteer studies due to the fact that PFC was lost from the circulation due to surgical bleeding occurring in these subjects.

TABLE IX

PFC Pharmacokinetic Parameters after Administration of Formulation of Ex. VI to Subjects Undergoing Noncardiac Surgery

| | Emulsion Dose | | | |
|---|---|---|---|---|
| | | 0.9 g PFC/kg | | 1.8 g PFC/kg |
| Parameter | n | Mean ± SD | n | Mean ± SD |
| Perflubron | | | | |
| $C_{max}$ (mg/L) | 36 | 7,685 ± 2,419 | 60 | 17,460 ± 6,252 |
| $AUC_\infty$ (h · mg/L) | 23 | 13,265 ± 8,617 | 35 | 57,351 ± 38,489 |
| $T_{1/2}$ (h) | 23 | 2.36 ± 3.06 | 35 | 3.77 ± 2.69 |
| CL (mL/h/kg) | 23 | 96.5 ± 59.1 | 35 | 42.2 ± 24.5 |
| PFDB | | | | |
| $C_{max}$ (mg/L) | 36 | 284 ± 92.7 | 60 | 620 ± 158 |
| $AUC_\infty$ (h · mg/L) | 27 | 736 ± 483 | 30 | 2,949 ± 2,166 |
| $T_{1/2}$ (h) | 27 | 2.73 ± 1.32 | 30 | 5.56 ± 4.81 |
| CL (mL/h/kg) | 27 | 58.4 ± 36.6 | 30 | 35.7 ± 37.0 |

PFDB = perfluorodecyl bromide; n = number of subjects with sufficient data for analysis. $C_{max}$ = maximum whole blood concentration; $AUC_\infty$ = area under the whole blood concentration-time curve to infinity; $t_{1/2}$ = elimination half-life; CL = whole blood clearance.

Example XII

Pharmacokinetics of the Formulation of Example VI in Subjects Undergoing Cardiac Surgical Procedures The pharmacokinetics of PFOB and PFDB were determined after the administration of the fluorocarbon formulation taught in Example VI to human subjects undergoing coronary artery bypass grafting or CABG surgery with hypothermic cardiopulmonary bypass. In group 1 and in group 2, human subjects received the fluorocarbon emulsion (2.7 g PFC/kg) as taught in Example VI directly into the bypass oxygenator after being put on bypass but before cooling was begun. In group 4, subjects received 2.7 g PFC/kg of the fluorocarbon emulsion of Example VI directly into the bypass oxygenator either prior to aortic cannulation or after being put on bypass, but before cooling was begun. The pharmacokinetic parameters for PFOB and PFDB are summarized in Table X.

TABLE X

PFC Pharmacokinetic Parameters After Administration of 2.7 g PFC/kg of Ex. VI Emulsion to Subjects Undergoing CABG Surgery with Hypothermic CPB

| Parameter | n | Mean ± SD |
|---|---|---|
| PFOB | | |
| Cmax (mg/L) | 36 | 30,305 ± 7,189 |
| $AUC_\infty$ (h · mg/L) | 34 | 300,233 ± 107,860 |
| $T_{1/2}$ (h) | 34 | 7.65 ± 2.71 |
| CL (mL/h/kg) | 34 | 9.88 ± 3.66 |

TABLE X-continued

PFC Pharmacokinetic Parameters After Administration
of 2.7 g PFC/kg of Ex. VI Emulsion to Subjects
Undergoing CABG Surgery with Hypothermic CPB

| Parameter | n | Mean ± SD |
|---|---|---|
| PFDB | | |
| Cmax (mg/L) | 36 | 1,031 ± 190 |
| $AUC_\infty$ (h · mg/L) | 33 | 16,234 ± 7,873 |
| $t_{1/2}$ (h) | 33 | 10.8 ± 4.46 |
| CL (mL/h/kg) | 33 | 6.75 ± 3.02 | n = Number of subjects with sufficient data for analysis.
Cmax = maximum whole blood concentration; $AUC_\infty$ = area under the whole blood concentration-time curve to infinity; $t_{1/2}$ = elimination half-life; CL = whole blood clearance.

Whole blood concentrations of perflubron were ~30-fold higher than those of PFDB, consistent with their relative proportions in the administered formulation (58% w/v PFOB/2% w/v PFDB). Administration of the fluorocarbon emulsion of Ex. VI prior to aortic cannulation or after initiation of CPB resulted in comparable whole blood concentrations and pharmacokinetic parameters for both PFOB and PFDB.

Example XIII

A Multicenter, Single-Blind, Randomized, Controlled, Parallel-Group Study of the Effectiveness of 2.7 g PFC/kg of a 58% PFOB/2% PFDB Fluorocarbon Emulsion as Taught in Example VI Combined with Acute Normovolemic Hemodilution Versus Standard Transfusion Practice (Control) in Reducing or Avoiding Transfusion of Stored Blood in Elective, Noncardiac Surgical Procedures Associated with Moderate-to-Large Volume Blood Loss The primary objective of this study was to evaluate whether augmented acute normovolemic hemodilution using the 58% PFOB/2% PFDB w/v fluorocarbon emulsion of Example VI as a temporary oxygen carrier could reduce transfusion of stored blood in humans, i.e., allogeneic RBC and/or Preoperative Autologous Donation (PAD) units in subjects undergoing elective, noncardiac surgical procedures associated with moderate-to-large-volume (≥20 mL/kg) blood loss compared to standard transfusion practice (Standard of care/SOC control).

Study Design

This was a Phase 3, single blind, randomised, parallel-group, controlled, multicenter study conducted at 34 clinical trial sites. A total of 492 patients undergoing major non-cardiac surgical procedures with expected blood, loss between 20 and 70 mL/kg were enrolled in the study. Additional key inclusion criteria included preoperative hemoglobin concentration [Hb] between 12 and 15 g/dL; 18 to 80 years of age; weight from 50 to 125 kg; American Society of Anaesthesiologists (ASA) physical status I-III; and estimated blood volume sufficient to allow removal of 2 units of autologous blood during preoperative acute normovolemic hemodilution ("ANH"). Operative procedures were to include primarily major cancer surgery (e.g., pelvic exenteration, "debulking" procedures for intra-abdominal tumors, excision of musculoskeletal tumors of the pelvis and extremities, major head and neck resections, liver resections, and removal of spinal cord tumors), bilateral and revision of hip arthroplasty, open reduction and internal fixation of pelvic fractures, and major vascular surgery. Blood salvage was not allowed in this study. Subjects were to be randomised before surgery to one of two study groups, study group 1 (ANH plus the fluorocarbon formulation of Example VI) or study group 2, Control, standard fusion practice (SOC).

Patients were transfused with blood using PAD units, if available, and allogeneic blood for each intraoperative transfusion trigger, i.e., either a protocol-defined [Hb] or any one of several protocol-defined intraoperative physiologic triggers. These included tachycardia (heart rate≥100 bpm or ≥135% of post anaesthesia induction value), hypotension (MAP≥60 mm Hg or ≥65% of post-induction value), P$\bar{v}O_2$≤38 mm Hg (if a pulmonary artery catheter was used), or ST-segment depression (>0.1 mV) or elevation (>0.2 mV).

A. Control Group (SOC):

The Control group was treated with standard transfusion practices as defined in a standard blood profusion protocol. They received transfusion with PAD units, if available, then allogeneic RBCs for each intraoperative [Hb] transfusion trigger of 8.0±0.5 g/dL and/or when at least one of the physiological triggers occurred. The Fraction of Inspired Oxygen (FIO$_2$) was maintained at 40% (FiO$_2$=0.4) for the duration of surgery (a level typically used in general surgery).

B. Treatment Group with the Fluorocarbon Emulsion of Example VI:

Prior to surgical incision, patients underwent ANH to [Hb] of 8.0±0.5 g/dL at a FiO$_2$=1.0, immediately followed by a 1.8 g PFC/kg intravenous dose (3 mL/kg) of the fluorocarbon emulsion of Example VI. When [Hb] reached 6.5±0.5 g/dL during surgery, a further 0.9 g PFC/kg (1.5 mL/kg) dose of the Example VI fluorocarbon emulsion was administered. Below a [Hb] of 5.5±0.5 g/dL or when any physiologic trigger (described above) was met, patients were to be transfused with ANH units and PAD blood, if available, before receiving allogeneic blood. All ANH blood was to be infused after surgery.

In both groups, a [Hb]≥8.5±0.5 g/dL was targeted at the end of surgery, maintained through postoperative day (POD) 3, and was required by protocol at hospital discharge. The ranges in [Hb] transfusion triggers (±0.5 g/dL) were not applicable for individual patients, but were provided to allow centres to adjust transfusion decisions (equally in both groups) according to local standards.

Evaluation of Efficacy

Endpoints:

The primary efficacy endpoint was the number of allogeneic and/or PAD units transfused during the acute study period (24 hours from skin incision). Secondary endpoints included: (1) percentage of subjects avoiding allogeneic RBC transfusions during the acute study period; (2) percentage of subjects avoiding allogeneic RBC and PAD unit transfusions during the acute study period; and (3) elapsed time from arrival in the recovery room to day of hospital discharge (DD) or POD 21. The primary efficacy population was defined as the intent-to-treat, which included all randomised subjects. A secondary protocol-defined efficacy population included all randomised subjects with estimated blood loss≥20 mL/kg.

Results:

Patient demographics were similar in both groups at screening and at baseline, as were types of surgeries. A total of 14 treated patients and 10 controls were withdrawn before treatment or surgery, either at their request or because clinical condition did not warrant surgery at the time. During preoperative ANH, 1,618 (SD=558 mL, range: 450-3,374 mL) of blood was withdrawn and replaced by 1,312 ml (SD=680 mL, range: 100-3,500 mL) of colloid and 2,418 (SD=1627 mL, range: 100-10,000 mL) crystalloid infusions. The post-ANH [Hb] was 8.1±0.5 g/dL. Of the 227 fluorocarbon emulsion treated patients, 50 received only the initial 1.8 g PFC/kg dose of the fluorocarbon emulsion of Example VI and never reached the second [Hb] trigger for dosing, while 177 subjects received the full 2.7 g PFC/kg dose.

In the intent-to-treat population (N=492), the primary endpoint (reduction in number of allogeneic/PAD units transfused at 24 hours) was achieved: the fluorocarbon emulsion group required fewer transfusions than controls (1.5 vs. 2.1 units, respectively), representing a reduction rate of 26% (Table XI, despite a higher intraoperative blood loss [2.7±2.7 L vs. 2.3±2.0 L; p<0.05]). However, in the protocol-defined target population (blood loss≥20 mL/kg; N=330 or 67% of randomised subjects), the fluorocarbon emulsion treated group had a higher mean rate of reduction (>40%) on POD 1 (Table XII). This difference remained significantly different from Controls through discharge (mean difference of 3.4 vs. 4.9 units at POD 21/DD; median difference of 2 vs. 4 units; p<0.001). In total, through POD 21/DD, the fluorocarbon emulsion treated subjects required 696 units versus 846 units in the Control group, representing a net savings of 150 units of allogeneic blood.

Figure 9A:
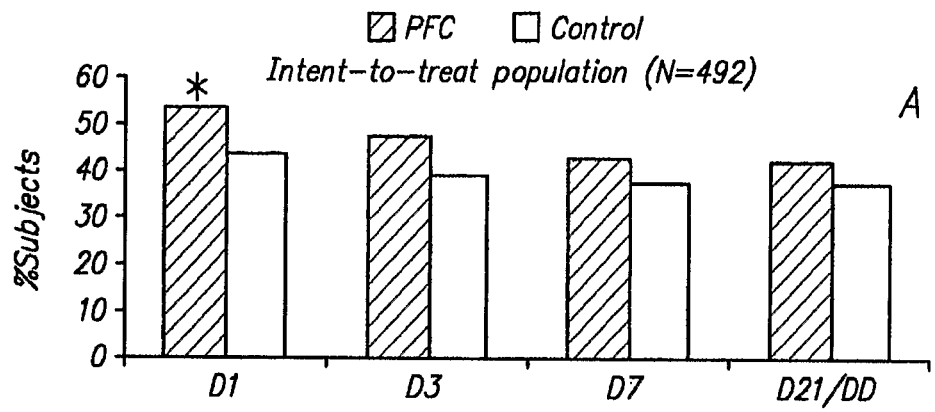
FIG. 9 shows the percent of subjects avoiding any allogeneic and PAD transfusions in (Panel A) the intent-to-treat population (N=492), (Panel B) the protocol-defined target population with blood loss≥20 mL/kg (N=330), and (Panel C) the clinical benefit group (post-hoc analysis), i.e. patients with surgical blood loss≥10 mL/kg (N=424). (*p<0.05 between groups)
Figure 9B:
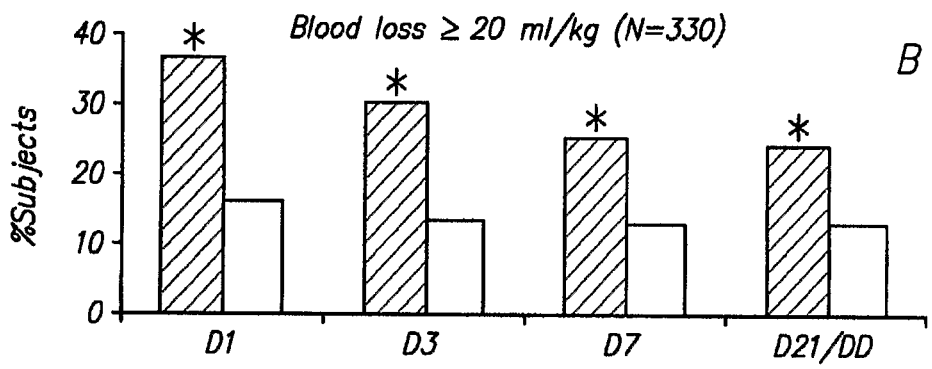
Figure 9C:
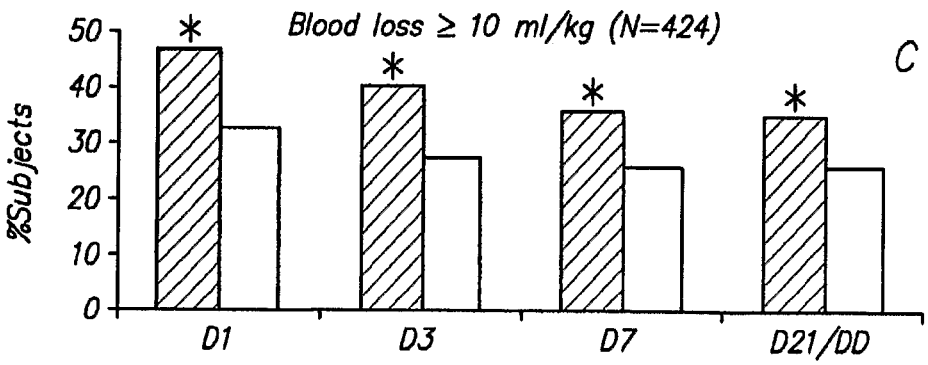

With respect to avoidance of transfusion in the intent-to-treat population (FIG. 9, Panel A), ~21% more subjects in the fluorocarbon emulsion treated group avoided allogeneic and PAD transfusions compared to Controls (p<0.05) during the acute study period (24 hours). In the protocol-defined target population, a significantly (p<0.05) greater percentage (almost twice as many) of subjects avoided transfusion at all time points from POD 1 through POD 21/DD (FIG. 9, Panel B). A post hoc analysis, conducted to identify all subjects that benefited from the fluorocarbon emulsion treatment, indicated that when surgical blood loss was ≥10 mL/kg (N=424; 86% of all subjects), transfusion was significantly reduced in the fluorocarbon emulsion-treated patients versus Controls (FIG. 9, Panel C).

Example XIV

Safety was evaluated for the fluorocarbon emulsion of Example VI on the basis of adverse event ("AE") reporting (including physical examination), incidence of infections, vital signs (heart rate, blood pressure, and body temperature), and clinical laboratory values (haematology, coagulation, and blood chemistries). Safety follow-up was performed by telephone to patients 3 months after surgery. An independent DSMB was used to periodically review laboratory and safety data during the conduct of this study.

Adverse events ("AEs") and serious adverse events ("SAEs") reported in this study were expected, as these subjects were undergoing major surgery with substantial blood loss. Table XIII presents AEs and SAEs. Overall, the incidence of all AEs was similar in the fluorocarbon emulsion treated group (86%) compared to Controls (81%), although

TABLE XI

Number of Allogeneic RBC and/or PAD Units Transfused
Intent-to-Treat Population

| Study Day | Treated (N = 241) Mean* | Control (N = 251) Mean* | Decrease from Control | Treated (N = 241) Median | Control (N = 251) Median | P Value[†] |
|---|---|---|---|---|---|---|
| Day 1 | 1.5 | 2.1 | 26.1% | 0 | 1 | 0.013 |
| Day 3 | 2.1 | 2.6 | 19.5% | 1 | 2 | 0.052 |
| Day 7 | 2.5 | 3.0 | 15.9% | 1 | 2 | 0.128 |
| Day 21 or DD[‡] | 2.7 | 3.2 | 15.5% | 1 | 2 | 0.162 |

*Adjusted mean from an analysis of covariance using a natural log transformation.
[†]Calculated using a linear model on ranks, comparing mean ranks.
[‡]POD 21 or Day of Discharge, whichever occurred sooner.

TABLE XII

Number of Allogeneic RBC and/or PAD Units Transfused
Target Population (Blood loss ≥20 mL/kg)

| Study Day | Treated (N = 178) Mean* | Control (N = 152) Mean* | Decrease from Control | Treated (N = 178) Median | Control (N = 152) Median | P Value[†] |
|---|---|---|---|---|---|---|
| Day 1 | 2.0 | 3.3 | 40.8% | 1 | 3 | <0.001 |
| Day 3 | 2.7 | 4.1 | 33.2% | 2 | 3 | <0.001 |
| Day 7 | 3.2 | 4.6 | 30.3% | 2 | 4 | <0.001 |
| Day 21 or DD[‡] | 3.4 | 4.9 | 30.3% | 2 | 4 | <0.001 |

*Adjusted mean from an analysis of covariance using a natural log transformation.
[†]Calculated using a linear model on ranks, comparing mean ranks.
[‡]POD 21 or Day of Discharge, whichever occurred sooner.

more AEs were reported in the fluorocarbon emulsion treated group for the categories "Body as a Whole", "Cardiovascular System" (hypertension) and "Digestive System" (ileus). Hypertension occurred mainly postoperatively and was likely related to the re-infusion of ANH blood. The clinical consequences in the ileus cases were minor, and no general pattern or pathophysiological mechanism was found in post hoc analyses that could link these events to treatment with the fluorocarbon emulsion of Example VI.

TABLE XIII

Adverse and Serious Adverse Events Through 3 Months Postdosing with Fluorocarbon Emulsion (Listed by COSTART Body System)

| Adverse Events | Treated (N = 227)* | Control (N = 241)* |
|---|---|---|
| Any Adverse Event† | 195 (86%) | 195 (81%) |
| Body as a Whole | 114 (50%) | 110 (46%) |
| Cardiovascular System | 90 (40%) | 73 (30%) |
| Digestive System | 101 (45%) | 84 (35%) |
| Haemic and Lymphatic System | 72 (32%) | 68 (28%) |
| Metabolic and Nutritional Disorders | 101 (45%) | 91 (38%) |
| Urogenital System | 51 (23%) | 62 (26%) |
| Any Serious Adverse Event‡ | 72 (32%) | 51 (21%) |
| Body as a Whole | 32 (14%) | 25 (10%) |
| Cardiovascular System | 16 (7%) | 12 (5%) |
| Digestive System | 16 (7%) | 5 (2%) |
| Metabolic and Nutritional Disorders | 7 (3%) | 5 (2%) |
| Musculoskeletal System | 4 (2%) | 3 (1%) |
| Urogenital System | 9 (4%) | 5 (2%) |
| Mortality | 10 (4%) | 5 (2%) |

*Treated randomised subjects (undergoing surgery and if in Treated group, also received the 1st dose of fluorocarbon emulsion).
†Adverse events reported in >5% of subjects in either the Treated or the Control group.
‡Serious adverse events reported in >1% of subjects in either the Treated or the Control group.

The difference in the overall incidence of SAEs between groups was significant (fluorocarbon emulsion 32% vs. Control, 21%; p=0.03). However, only the category "Digestive System" was statistically different from Control, mostly due to a higher occurrence of postoperative ileus, as noted above. Four SAE cases of ileus were reported in the fluorocarbon emulsion treated group (versus none in Controls); one after a rectum amputation, two following major gynaecological tumour excision and one after radical cystectomy. The low incidence of reports of ileus in this patient population is surprising, as the vast majority of the patients were undergoing abdominopelvic surgery, this suggests a degree of underreporting, particularly in the Control group. The incidence, nature and time course of postoperative morbidity in both groups were consistent with the published literature for patients undergoing extensive non-cardiac surgical procedures for malignancies, and nothing suggesting any effect of the fluorocarbon emulsion was observed. Aggregates of all infectious complications were similar in both groups at 32%, supporting earlier clinical findings that immune function was not compromised by the fluorocarbon emulsion.

As noted previously, the fluorocarbon emulsion treated group underwent moderate preoperative ANH (an average of ~30% of blood volume was withdrawn and should have been replaced simultaneously with colloid and/or crystalloid solutions). There was evidence, however, that ANH may not always have been performed under normovolemic conditions in this particular example. Analyses indicated that in ~70% of fluorocarbon emulsion treated subjects, the volume of fluid administered was not appropriate for the volume of blood removed during ANH. In some subjects, inadequate fluid replacement might have resulted in hypoperfusion, which may not have been adequately corrected during the remainder of the operative period. Thus, certain fluorocarbon emulsion treated subjects may have been predisposed to greater postoperative morbidity, such as adverse events related to ischemia. In other subjects, excessive fluid replacement during ANH appeared to be associated with some complications more typical of circulatory overload. These analyses confirmed independent conclusions of the data safety monitoring board ("DSMB") monitoring this study, which noted some group imbalances in certain aggregated adverse events, suggesting that some patients may have been hypovolemic. However, the DSMB concluded that there was no clinically consistent pattern or significance and urged that further studies in general surgery populations be undertaken to confirm efficacy and to further evaluate the safety profile of the fluorocarbon emulsion of Example VI. Mortality was similar between groups (4% vs. 2%), and all deaths were considered to be unrelated to the study drug by the investigators. Instead, the deaths were considered to be due to natural tumour progression, sepsis, multi-organ failure, and cardiopulmonary complications. A transient decrease in platelet counts occurring a few days postsurgery was observed and was expected based on previous clinical data. As the number of platelet transfusions and the incidence of bleeding events were similar in both groups, it would appear that this moderate drop in postoperative platelet count is of little clinical relevance. This is consistent with earlier studies in human volunteers demonstrating no effect of PFC emulsion on platelet function and bleeding time.

Conclusions of Data in Examples XIII and XIV

This general surgery study was successful in demonstrating statistically significant reduction and avoidance of allogeneic blood and PAD transfusion in subjects undergoing a variety of major, general surgical procedures when infused with the fluorocarbon formulation of Ex. VI. Overall, the profile and incidence rate of postoperative morbidity was considered acceptable and largely unremarkable for both groups. Although there was a higher incidence of SAEs in the fluorocarbon emulsion treated group, the events observed were not unexpected for this elderly surgical population and were not attributed to the administered fluorocarbon emulsion by the investigators. Also, the single-blind nature of this particular study appears to have contributed to some under reporting of events in the Control group and perhaps a tendency to over report in the fluorocarbon emulsion treated group.

Example XV

A Phase 3, Single-Blind, Randomised, Parallel-Group, Multicenter, Controlled Study of the Effectiveness of 2.7 g PFC/kg of Fluorocarbon Emulsion of Example VI to Augment Intraoperative Autologous Donation and Avoid Transfusion of Allogeneic Red Blood Cells in Patients Undergoing Primary Coronary Artery Bypass Graft Surgery Under Cardiopulmonary Bypass The primary study objective was to evaluate the efficacy of the fluorocarbon emulsion of Example VI as a temporary oxygen carrier to avoid transfusion of allogeneic blood, by permitting more extensive harvesting of autologous blood immediately before cardiopulmonary bypass "CPB" in patients undergoing CABG procedures.

Study Design

This was a Phase 3, single-blind, randomised, parallel-group, multicenter, controlled study conducted at 38 clinical trial sites. Cardiac surgery patients, aged 18 to 80 years, scheduled for primary, nonemergent CABG surgery (not including valve surgery) under hypothermic or normothermic CPB were randomised prior to surgery into two groups: fluorocarbon emulsion treatment (ANH plus Intraoperative Autologous Donation [IAD]) or Control (ANH only). Additional key inclusion criteria included preoperative screening [Hb]≥11 and ≤14 g/dL; weight from 50 to 125 kg; and an ASA physical status classification of 2 or 3, or ASA 4 if due to unstable angina.

The study was intended to enrol 600 human subjects (300 per study group). A total of 411 subjects (205 Treated and 206 Control) were enrolled in the study at 38 clinical trial sites. Before initiating bypass, the anaesthesiologist performed ANH to target a [Hb] that would result in an initial on-bypass [Hb] of 8 g/dL; the same degree of ANH was to be performed in both fluorocarbon emulsion and Control subjects. In the fluorocarbon emulsion treated group, IAD (a technique whereby autologous blood from the patient is collected just as CPB is being started) was performed by the perfugionist just before initiating bypass to target a lower on-bypass [Hb] (6 g/dL) than Control subjects and to reserve additional autologous blood. Blood collected by ANH and IAD was to be simultaneously replaced by starch-based colloid, albumin, and/or crystalloid in adequate amounts to ensure normovolemia. The initial bypass flow rate (BFR) was set at 2.2 to 2.4 L/min/m$^2$ under normothermic conditions (35 to 37° C.) with maximal oxygenation of arterial blood maintained via the oxygenator (i.e., 100% $O_2$) in both groups. During hypothermic bypass (temperature range of 28 to 34° C.), the BFR was decreased to 1.8 to 2.0 L/min/m$^2$. Intraoperative autologous blood salvage (ABS) was allowed in both groups.

In both groups, subjects were transfused when protocol-specified [Hb] or physiologic triggers were reached. However, transfusion in response to physiologic triggers was not mandatory when [Hb] was ≥10 g/dL in the intraoperative period. The BFR could be changed if dictated by clinical need, but was not to be increased for the purpose of trying to correct the protocol-defined physiologic transfusion triggers. These included $P\bar{v}O_2$≤30 mm Hg during hypothermic CPB (≤35 mm Hg when normovolemic CPB was used), $S\bar{v}O_2$≤65%, and ST-segment depression (≥0.1 mV) or elevation (≥0.2 mV).

Fluorocarbon Emulsion Treatment Group:

Subjects in the fluorocarbon emulsion treatment group received the first intravenous ("IV") dose of the fluorocarbon emulsion as described in Example VI (1.8 g PFC/kg; 3.0 mL/kg) immediately prior to going onto bypass. A second dose of the fluorocarbon emulsion of Example VI (0.9 g PFC/kg; 1.5 mL/kg) was administered IV immediately following IAD collection as bypass was being initiated. Subjects were transfused with ANH and IAD blood (and PAD units, if available), before receiving allogeneic red cells according to the protocol-defined [Hb] triggers (i.e., 5.5 g/dL on-bypass and 7.0 g/dL immediately postbypass) and/or when any of the physiological triggers (described above) occurred.

Control Group:

Control subjects received a volume-matched IV infusion (3 mL/kg) of a balanced electrolyte solution after the last ANH unit was removed, followed by an additional 1.5 mL/kg as bypass was being initiated. Subjects were transfused with ANH units (and PAD units, if available) before receiving allogeneic blood for each intraoperative [Hb] transfusion trigger (i.e., 7.0 g/dL on-bypass and 8.0 g/dL immediately post-bypass) and/or when any of the physiological triggers (described above) occurred.

In the immediate post-bypass period, autologous blood was administered to maintain hemodynamic stability in both groups. Autologous blood, followed by allogeneic RBCs, was transfused when [Hb] or physiologic triggers were reached. All available ANH units and IAD blood were to be returned to the subject before leaving the operating room, unless contraindicated. In the postoperative period (through POD 7 or DD, whichever occurred sooner), allogeneic RBCs were to be transfused to maintain [Hb]>8.0 g/dL, or earlier if physiologic triggers ($P\bar{v}O_2$ and $S\bar{v}O_2$ through 24 hours postsurgery only) were observed that could not be reversed by routine intervention.

Evaluation of Efficacy

Endpoints:

The primary efficacy endpoint was the proportion of subjects who avoided allogeneic RBC transfusion in the fluorocarbon emulsion treated group compared to the Control group through POD 7 or DD, whichever occurred sooner. The secondary efficacy endpoint was the number of allogeneic RBC units transfused through POD 7 or DD (whichever occurred sooner).

Evaluation of Safety

Endpoints:

Safety was assessed on the basis of adverse events, vital signs, clinical lab values, and physical examination. Duration of mechanical ventilation, time in the ICU, duration of hospital stay, reoperation for postoperative bleeding, and the incidence of postoperative myocardial infarction (MI), stroke, and renal failure were also to be assessed during the acute study period. A safety follow-up by telephone to assess any adverse events was also performed 3 months after surgery. An independent DSMB was used to periodically review safety data during the conduct of this study.

Results:

Because patient enrolment was suspended, an interim safety analysis was performed using all available data from the 398 subjects (200 fluorocarbon emulsion treated patients and 198 Control patients) in this study to investigate the aetiology of imbalances in the incidence of cerebrovascular accidents (CVAs) and postoperative bleeding events between the fluorocarbon emulsion treated groups and Control groups. The remaining 13 subjects (5 fluorocarbon emulsion and 8 Control) were withdrawn prior to study and did not receive the assigned protocol treatment.

AEs were reported for all subjects enrolled in the study, as expected in this patient population. Protocol-specified analyses indicated no statistically significant differences in the overall incidence of AEs or SAEs between groups. The incidence of SAEs (34.4% overall; fluorocarbon emulsion treated, 38.5%; Control, 30.3%) and deaths (1.5% overall; fluorocarbon emulsion treated 2.5%; Control 0.5%) were generally within published ranges expected up to 3 months post-CABG surgery involving CPB, although the 0.5% mortality in the Control group was exceptionally low (refer to Table IX. A recent publication involving a large cohort of patients undergoing CABG surgery involving CPB reported a mortality rate of 4.5%. Klein M, Mahoney et al, "Blood product use during routine open heart surgery: The impact of the centrifugal pump." *Artificial Organs* 25(4):300-305 (2001).

Analysis of other protocol-defined safety outcomes including extensive laboratory investigations up to the day of hospital discharge, showed little evidence of medically important untoward effects. In essence, the nature and time course of postoperative morbidity reported in this study were consistent with historical data for this CABG population.

TABLE XIV

Adverse and Serious Adverse Events Through 3 Months Postdosing (Listed by COSTART Body System)

| Adverse Events | Emulsion (N = 200)* | Control (N = 198)* |
|---|---|---|
| Any adverse event† | 200 (100%) | 198 (100%) |
| Body as a Whole | 196 (98%0 | 198 (100%) |
| Cardiovascular System | 183 (93%) | 167 (84%) |
| Digestive System | 146 (73%) | 142 (72%) |
| Haemic and Lymphatic System | 94 (47%) | 76 (38%) |
| Metabolic and Nutritional Disorders | 151 (76%) | 148 (75%) |
| Nervous System | 124 (62%) | 95 (48%) |
| Respiratory System | 177 (89%) | 170 (86%) |
| Urogenital System | 69 (35%) | 47 (24%) |
| Any serious adverse event‡, | 80 (40%) | 61 (31%) |
| Body as a Whole | 14 (7%) | 12 (6%) |
| Cardiovascular System | 47 (24%) | 28 (14%) |
| Digestive System | 8 (4%) | 5 (3%) |
| Haemic and Lymphatic System | 5 (3%) | 3 (2%) |
| Metabolic and Nutritional Disorders | 5 (3%) | 4 (2%) |
| Nervous System | 17 (9%) | 3 ((2%) |
| Respiratory System | 22 (11%) | 22 (11%) |
| Urogenital System | 6 (3%) | 0 (0%) |
| Mortality | 5 (2.5%) | 1 (0.5%) |

*Treated randomised subjects (undergoing surgery and if in Fluorocarbon Emulsion group, also received the first dose of).
†Adverse events reported in >10% of subjects in either the Oxygent or the Control group.
‡Serious adverse events reported in >1% of subjects in either the Oxygent or the Control group.

The overall incidence rates for serious neurological and bleeding complications were within the ranges normally reported in the literature; however, the rates in the Control group were exceptionally low. Typically, adverse neurological outcomes, either focal or global, occur in approximately 2% to 6% of patients undergoing CABG and approximately 2% of CABG patients require reoperation for intrathoracic hemorrhage. The reasons for the higher than expected rates of neurological and bleeding events in the fluorocarbon emulsion group were the subject of extensive post hoc exploratory analyses and hypothesis generation.

Procedural variables appear to have increased the risk of neurological events. Subjects randomized to the fluorocarbon emulsion treated group underwent ANH (average of 9.5% of blood volume removed) and had additional blood removed—sometimes very rapidly—via IAD (average of 18.4% of blood volume). The total volume of autologous blood withdrawn (ANH plus IAD) proved to be a significant risk factor for serious neurological complications: an average of 330 mL more autologous blood was withdrawn using the combined blood harvesting procedures in subjects for whom serious neurological events were reported compared to those for whom they were not. The more common use of vasopressors (to support perfusion pressure) in fluorocarbon emulsion treated subjects suggests that they may have been hypotensive as they were going onto bypass (i.e., secondary to rapid removal of large volumes of blood, potentially in the absence of adequate fluid replacement), and helps to support the hypothesis that a hypoperfusion/hypoxic episode occurred during IAD resulting in an oxygen debt, the effects of which continued for many hours and likely exacerbated postoperative morbidity.

TABLE XV

ANH and IAD Volume Withdrawn (in mL or as a Percentage of Blood Volume)

| ANH and/or IAD Volume Withdrawn | Statistics | PFC Emulsion N = 200 | Control N = 198 |
|---|---|---|---|
| Total ANH volume withdrawn (mL) | Mean (SD) | 518 (368) | 504 (344) |
| ANH volume (% blood volume) | Mean (SD) | 9.5 (6.1) | 9.5 (6.1) |
| Total IAD volume withdrawn (mL) | n | 166 | 2 |
| | Mean (SD) | 1037 (484) | 352 (214)* |
| | Min, Max | 104, 2637 | 200, 503 |
| IAD volume (% blood volume) | n | 166 | 2 |
| | Mean (SD) | 18.4 (7.6) | 6.5 (2.1)* |
| | Min, Max | 2, 41 | 5, 8 |
| Total ANH + IAD volume (mL) | Mean (SD) | 1379 (792) | 507 (348) |
| | Min, Max | 300, 3600 | 220, 2700 |
| Total ANH + IAD volume (% blood volume) | Mean (SD) | 24.7 (12.8) | 9.6 (6.1) |
| | Min, Max | 4, 64 | 4, 47 |

*Two Control subjects had IAD performed. The protocol allowed this in Control subjects if the ANH procedure could not be continued for some reason and the remainder of the "ANH blood" needed to be removed.

In the fluorocarbon emulsion treatment group, the time between IAD withdrawal and return of IAD blood and the volume of hetastarch used were notable independent risk factors for bleeding complications. It is hypothesized that a dilutional coagulopathy due to the large volume of IAD blood harvested and a greater volume of hetastarch use, combined with the return of IAD blood with high heparin concentration at the end of surgery, exacerbated the hemostatic dysfunction already caused by heparinization and CPB.

In the Control group, procedural variables also may have played a role in the remarkably low incidence of serious neurological and bleeding complications. The moderate degree of ANH (target initial on-bypass [Hb]=8.0 g/dL) and the administration of 100% oxygen during the procedure may have improved patient outcome: the former by decreasing blood viscosity and improving microvascular flow, and the latter by increasing the amount of oxygen available and enabling an improved degree of extraction by the tissues. In addition, fresh autologous blood, not exposed to the deleterious effects of the bypass circuit, was available for transfusion in the post bypass period.

Several other factors may also have confounded the safety of this study, particularly, the lack of standardization of important procedural aspects of patient management across investigational sites, as well as a lack of prospectively established definitions of laboratory and clinical parameters to standardize adverse event reporting. Most importantly, the results of this investigation indicate that the administration of the fluorocarbon emulsion of Example VI per se did not appear to have increased the risk of neurological or bleeding events. Additionally, laboratory ex vivo investigations showed no evidence of meaningful physical or chemical interactions or incompatibility between the fluorocarbon emulsion of Example VI and either blood, colloid, or other common reagents and drugs used during CPB (e.g., heparin); furthermore, there were no effects on shear-dependent viscosity measurements in these mixtures. Likewise, detailed retrospective review of pharmacology and toxicology studies relating to hemostasis and the CNS failed to reveal evidence of an effect of PFC-based emulsions in various models.

Example XVI

Clinical Studies in Human Patients Undergoing General Surgery

Subjects undergoing orthopedic surgery (N=147) were enrolled in the first study, and subjects undergoing genitourinary surgery (N=99) were enrolled in a second study. As the studies were almost identical, a combined summary is provided below.

Objectives/Study Design: The objectives of these randomized, multicenter, controlled, single-blind, parallel-group studies were to evaluate the safety and efficacy of a single intravenous infusion of the fluorocarbon emulsion of Example VI (0.9 or 1.8 g PFC/kg) plus an $FiO_2$ of 1.0 relative to either blood plus $FiO_2$=0.4 or colloid plus $FiO_2$=1.0 following ANH in patients undergoing orthopedic (hip replacement or spinal surgery) or genitourinary (radical prostatectomy, radical hysterectomy, or cystectomy) surgery. A total of 246 subjects (109 treated with fluorocarbon emulsion and 137 treated with colloid or blood [Control group]) were randomized in these studies.

Efficacy endpoints included the reversal of physiologic transfusion triggers and the duration of reversal. Safety was assessed based on incidence of adverse events, clinical laboratory tests (hematology, blood chemistries, and coagulation), and vital signs through 28 days post surgery.

Safety Results: The overall incidence of adverse events in these studies was comparable for the 1.8 g PFC/kg (66%) group relative to the Blood Control (68%) and Colloid Control (61%) groups; the incidence of adverse events in subjects who received 0.9 g PFC/kg (50%) was lower than all other groups. In general, adverse events were mild to moderate in severity and typical of postoperative morbidity in the surgical populations studied. None of the events resulted in withdrawal of the subjects from the study.

No subject died during or within 30 days following the study period in either of the studies. There were no clinically meaningful differences between the fluorocarbon emulsion and Control groups in the incidence or types of serious adverse events reported, and the incidence was greatest for the Colloid Control group (18%, 13 subjects) relative to all other treatment groups (5% [n=2], 11% [n=8], and 9% [n=6] for the fluorocarbon emulsion 0.9 g PFC/kg, 1.8 g PFC/kg, and Blood Control groups, respectively). All serious adverse events were judged by the investigator to have had an unlikely relationship to study drug.

Abnormal laboratory values appeared to be related to the surgical and hemodilution procedures rather than to study drug. In both studies, a transient decrease in platelet count was observed in the fluorocarbon and Control groups on Day 2 through Day 3. The nadir of this drop in platelet count was observed on Day 2 in both studies and differed little between groups. By Day 28, following a sizable overcompensation that is an expected acute phase response to surgery, platelet count returned to near baseline levels for all treatment groups. No clinically meaningful changes in vital signs or physical examination findings were noted.

Efficacy Results: The fluorocarbon emulsion of Example VI, at a dose of 1.8 g PFC/kg, was found to have a significantly higher proportion of subjects achieving reversal of transfusion triggers than the Blood Control in both studies (97% vs 60% and 69% vs 37% in first and second study, respectively). In addition, the duration of reversal (i.e., time from the start of treatment for the first transfusion trigger to the start of transfusion for the second transfusion trigger or the end of surgery) was significantly longer for subjects who received fluorocarbon emulsion 1.8 g PFC/kg relative to both Blood and Colloid Control groups (60 vs 30 min and 28 vs 15 min in the first study and second study, respectively). The fluorocarbon emulsion 0.9 g PFC/kg group also showed significantly longer duration of reversal than the Colloid Control group.

The fluorocarbon emulsion 1.8 g PFC/kg was also found to be significantly more effective than Blood Control in correcting the $PIO_2$ trigger at the first transfusion (87% vs 14% of subjects, respectively, only in second study). In addition, $FiO_2$ was cited as a second transfusion trigger for only two subjects (6%) in the fluorocarbon emulsion 1.8 g PFC/kg group versus 13 subjects (43%) in the Blood Control group. This would seem to indicate that fluorocarbon emulsion of Example VI is capable of sustaining $FiO_2$ levels in a majority of cases following treatment at the first transfusion trigger. The ability of the fluorocarbon emulsion of Example VI to increase $FiO_2$, reverse physiologic transfusion triggers, and delay the occurrence of subsequent triggers following administration, demonstrated the oxygen delivery properties of the fluorocarbon emulsion of Example VI.

Conclusion: A single infusion of the emulsion of Example VI at 1.8 g PFC/kg administered with $FiO_2$=1.0 was statistically better than either blood plus $FiO_2$=0.4 (second study only) or colloid plus $FiO_2$=1.0 with respect to both the duration of reversal and the proportion of subjects achieving reversal of transfusion triggers during moderate blood loss surgery accompanied by hemodilution. The fluorocarbon emulsion of Ex. VI at 0.9 g PFC/kg plus $FiO_2$=1.0 was statistically similar to treatment with blood plus $FiO_2$=0.4 with respect to these efficacy measures. A benefit with respect to the secondary endpoint of requirement for allogeneic blood was not seen in this study. Used in this surgical setting, the fluorocarbon emulsion of Example VI (0.9 and 1.8 g PFC/kg), showed an acceptable safety profile with only a mild, reduction in platelet count at 1.8 g PFC/kg.

The invention claimed is:

1. A fluorocarbon emulsion comprising: a continuous aqueous phase and a discontinuous fluorocarbon phase, wherein the discontinuous fluorocarbon phase consists of perfluorooctyol bromide and perfluorodecyl bromide, wherein the perfluorooctyl bromide is present in the fluorocarbon emulsion at 57-60% w/v of the total emulsion and the perfluorodecyl bromide is present in the emulsion at 1-3% w/v of the total emulsion.

2. The fluorocarbon emulsion of claim 1 further comprising an emulsifying agent consisting of egg yolk phospholipid present in the amount of 3.5%-4% w/v of the total emulsion.

3. The fluorocarbon emulsion of claim 1 wherein the emulsion is stabilized by a surfactant.

4. The fluorocarbon emulsion of claim 1 wherein the discontinuous fluorocarbon phase consists of 58-59% w/v perfluorooctyl bromide PFOB and 2-3% w/v perfluorodecyl bromide of the total emulsion PFDB.

5. The fluorocarbon emulsion of claim 1 wherein the discontinuous phase consists of 58% w/v perfluorooctyl bromide PFOB and 2% w/v perfluorodecyl bromide of the total emulsion PFDB.

6. The fluorocarbon emulsion of claim 1 wherein upon formation of the emulsion, fluorocarbon particles of a median particle diameter of 0.18 μm are formed.

7. The fluorocarbon emulsion of claim 1 further comprising a lecithin in the amount of 3-4% w/v of the total emulsion.

8. The fluorocarbon emulsion of claim 7 wherein the lecithin is egg yolk phospholipid and is present in the amount of 3.6% w/v of the total emulsion.

9. The fluorocarbon emulsion of claim 1 further comprising a chelator.

10. The fluorocarbon emulsion of claim 9 wherein the chelator is d,α-tocopherol.

11. The fluorocarbon emulsion of claim 1 wherein the perfluorooctyl bromide is present in the amount of 57-59% w/v of the total emulsion and the perfluorodecyl bromide is present in the amount of 2% w/v of the total emulsion.

* * * * *